(12) United States Patent
Alam

(10) Patent No.: US 10,420,770 B2
(45) Date of Patent: Sep. 24, 2019

(54) COMPOSITIONS AND METHODS FOR TREATING DEMENTIA

(71) Applicant: EIP Pharma, LLC, Cambridge, MA (US)

(72) Inventor: John Jahangir Alam, Cambridge, MA (US)

(73) Assignee: EIP Pharma, LLC, Cambridge, MA (US)

( * ) Notice: Subject to any disclaimer, the term of this patent is extended or adjusted under 35 U.S.C. 154(b) by 0 days.

(21) Appl. No.: 16/145,680

(22) Filed: Sep. 28, 2018

(65) Prior Publication Data

US 2019/0030035 A1    Jan. 31, 2019

Related U.S. Application Data

(63) Continuation of application No. PCT/US2017/029012, filed on Apr. 21, 2017.

(60) Provisional application No. 62/429,705, filed on Dec. 2, 2016, provisional application No. 62/325,892, filed on Apr. 21, 2016.

(51) Int. Cl.
*A61K 31/519* (2006.01)
*A61P 25/28* (2006.01)

(52) U.S. Cl.
CPC ............ *A61K 31/519* (2013.01); *A61P 25/28* (2018.01)

(58) Field of Classification Search
CPC ............................. A61P 25/28; A61K 31/519
See application file for complete search history.

(56) References Cited

U.S. PATENT DOCUMENTS

| 8,697,627 | B2 * | 4/2014 | Alam | C07D 403/12 514/1 |
| 9,427,438 | B2 * | 8/2016 | Alam | C07D 403/12 |
| 9,427,439 | B1 * | 8/2016 | Alam | A61K 31/519 |
| 9,579,322 | B2 * | 2/2017 | Alam | A61K 31/519 |
| 2005/0004167 | A1 | 1/2005 | Bora et al. | |
| 2007/0232632 | A1 | 10/2007 | Lucking et al. | |
| 2009/0203702 | A1 * | 8/2009 | Bemis | C07D 213/56 514/248 |
| 2012/0289511 | A1 * | 11/2012 | Alam | C07D 403/12 514/248 |
| 2016/0008364 | A1 | 1/2016 | Alam | |

FOREIGN PATENT DOCUMENTS

WO    WO-2017/185073 A1    10/2017

OTHER PUBLICATIONS

Woodford et al., Cognitive assessment in the elderly: a review of clinical methods. QJM. Aug. 2007;100(8):469-84. Epub Jun. 12, 2007. Review. PubMed PMID: 17566006. (Year: 2007).*
Arevalo-Rodriguez et al., Mini-Mental State Examination (MMSE) for the detection of Alzheimer's disease and other dementias in people with mild cognitive impairment (MCI). Cochrane Database Syst. Rev. Mar. 5, 2015;(3):CD010783. PubMed PMID: 25740785. (Year: 2015).*
Barrientos, R. M. et al, Time course of hippocampal IL-1 beta and memory consolidation impairments in aging rats following peripheral infection, Brain Behav. Immun., 23(1): 46-54 (2009).
Boon, B. D. C. et al, Non-Amnestic Alzheimer's Disease: A Possible Role for Neuroinflammation?, The Journal of the Alzheimer's Association, 13(7) Supplement: 1131-1132 (2017).
Burgess, N. et al, The Human Hippocampus and Spatial and Episodic Memory, Neuron, 35: 625-641 (2002).
International Search Report for PCT/US2017/029012, 3 pages (dated Jul. 24, 2017).
Lawrence, J., Alzheimer's will be treated with 'cocktail' of drugs, predicts neuroscientist, The Pharmaceutical Journal, 2 pages (2016).
Nixon, R. A., Endosome function and dysfunction in Alzheimer's disease and other neurodegenerative diseases, Neurobiology of Aging, 26: 373-382 (2005).
Teipel, S. J. et al, Predictors of cognitive decline and treatment response in a clinical trial on suspected prodromal Alzheimer's disease, Neuropharmacology, 108: 128-135 (2016).
Written Opinion for PCT/US2017/029012, 8 pages (dated Jul. 24, 2017).

* cited by examiner

*Primary Examiner* — Theodore R. West
(74) *Attorney, Agent, or Firm* — Wolf, Greenfield & Sacks, P.C.; Robert N. Sahr

(57) ABSTRACT

The present invention provides methods and compositions for improving episodic memory and treating dementia.

10 Claims, 19 Drawing Sheets

The mini mental state examination

Orientation
Year, month, day, date, season _____ /5
Country, county, town, hospital, ward (clinic) _____ /5

Registration
Examiner names three objects (for example, apple, pen, and table)
Patient asked to repeat objects, one point for each. _____ /3

Attention
Subtract 7 from 100 then repeat from result, stop after
five subtractions. (Answers: 93, 86, 79, 72, 65)
Alternatively if patient errs on subtraction get them to
spell world backwards: D L R O W
Score best performance on either task. _____ /5

Recall
Ask for the names of the objects learned earlier. _____ /3

Language
Name a pencil and a watch. _____ /2
Repeat: 'No ifs, and or buts.' _____ /1
Give a three stage command. Score one for each
stage (for example, 'Take this piece of paper in your right
hand, fold it in half and place it on the table.' _____ /3
Ask patient to read and obey a written command
on a piece of paper stating: 'Close your eyes.' _____ /1
Ask patient to write a sentence. Score correct if
it has a subject and a verb. _____ /1

Copying
Ask patient to copy intersecting pentagons.
Score as correct if they overlap and each has five sides. _____ /1

Total score: _____ /30

| MMSE Score | Mental Function |
|---|---|
| 27-30 | Normal Function |
| 21-26 | Mild Impairment |
| 11-20 | Moderate Impairment |
| 0-10 | Severe Impairment |

≥ 3 Point Change
Generally Considered
Clinically Significant

Figure 1

|  | 40 mg | 125 mg |
|---|---|---|
| Number randomized | 9 | 7 |
| Median age (range) | 68 (60-72) | 65 (60-75) |
| Gender (F:M) | 2:7 | 4:3 |
| Median weight (range) | 78 kg (63-97) | 67 kg (40-89) |
| Median MMSE (range) | 23 (20-28) | 24 (22-28) |

Figure 4

Number of subjects reporting adverse event by severity

| ADVERSE EVENT | 40 mg (N=9) | | 125 mg (N=7) | | Combined (N=16) | |
|---|---|---|---|---|---|---|
| | Mild | Moderate | Mild | Moderate | Mild | Moderate |
| Abdominal Pain | 0 | 1 | 1 | 0 | 1 | 1 |
| Aggression | 1 | 0 | 0 | 0 | 1 | 0 |
| Anemia | 1 | 0 | 0 | 0 | 1 | 0 |
| Ankle Fracture | 0 | 0 | 0 | 1 | 0 | 2 |
| Blood potassium increased | 0 | 1 | 0 | 0 | 0 | 1 |
| Diarrhea | 2 | 1 | 0 | 0 | 2 | 1 |
| Eczema | 0 | 0 | 1 | 0 | 1 | 0 |
| Hypothyroidism | 1 | 0 | 0 | 0 | 1 | 0 |
| Hot flush | 0 | 0 | 1 | 0 | 1 | 0 |
| Hypertension | 0 | 0 | 0 | 0 | 0 | 1 |
| Inappropriate Antidiuretic Hormone Secretion | 0 | 1 | 0 | 0 | 2 | 0 |
| Influenza like illness | 1 | 0 | 1 | 0 | 1 | 0 |
| Localized infection (Toe) | 1 | 0 | 0 | 0 | 1 | 0 |
| Malaise | 0 | 1 | 0 | 0 | 0 | 1 |
| Panic attack (MRI induced) | 0 | 1 | 0 | 0 | 0 | 1 |
| Rash (Exanthema of hands) | 0 | 0 | 1 | 0 | 1 | 0 |
| Respiratory tract infection | 0 | 0 | 0 | 1 | 0 | 1 |
| Snoring | 0 | 1 | 0 | 0 | 0 | 1 |
| Somnolence (sleepiness, drowsiness) | 1 | 0 | 1 | 0 | 2 | 0 |
| Spinal claudication | 1 | 0 | 0 | 0 | 1 | 0 |
| Vertigo Positional | 1 | 0 | 0 | 0 | 1 | 0 |

Figure 5

| | 40 mg | Overall Study |
|---|---|---|
| Number randomized | 8 | 9 |
| Median age (range) | 71 (66-74) | 71 (66-74) |
| Gender (F:M) | 5:3 | 5:4 |
| Median weight (range) | 64 kg (52-101) | 64 kg (52-101) |
| Median MMSE (range) | 25 (23-28) | 25 (23-28) |
| Median Baseline CSF Aβ1-42 (range; pg/ml) | 370 (130-612) | 350 (130-612) |

Figure 10

COMPOSITIONS AND METHODS FOR TREATING DEMENTIA

CROSS REFERENCE TO RELATED APPLICATIONS

The present application is a Continuation of International Application No. PCT/US17/29012, filed Apr. 21, 2017, which claims the benefit of U.S. Provisional Application No. 62/325,892, filed Apr. 21, 2016, and U.S. Provisional Application No. 62/429705 filed Dec. 2, 2016, each of which are hereby incorporated by reference in their entireties.

BACKGROUND

Dementia is a category of brain disease which is characterized by a long term, often gradual, decrease in a person's memory or other thinking skills that is great enough to affect daily functioning. Common causes of dementia include Alzheimer's disease, vascular dementia, Lewy body dementia, and frontotemporal dementia. A person may suffer from more than one type of dementia.

While symptoms can vary greatly, diagnosis of dementia can be made when one or more of the following core mental functions are significantly impaired; memory, communication and language, ability to focus and pay attention, reasoning and judgment, and visual perception. Health care costs for dementia have been found to be greater than that of any other disease. According to the National Institutes of Health, total spending for people with dementia in the last five years of life was more than a quarter-million dollars per person.

The types of memory systems that may be affected by dementia include episodic memory, semantic memory, simple classical conditioning, procedural memory, working memory, and priming (Gold, C. A. and Budson, A. E. "Memory loss in Alzheimer's disease: implications for development of therapeutics," Expert Rev. Neurother. 8(12):1879-91 (2008)). Each of these types of memory systems may be differentially affected depending on disease. Episodic memory facilitates individuals to remember events, times and places acquired through personal experience. Impairment of episodic memory is often one of the earliest signs and symptoms of dementia and directly linked to pathologic lesions within the hippocampus, a critical region of the brain for episodic memory formation. Of the memory systems most authors consider the episodic memory system to be the most clinically relevant for dementia, as impairments in this system can worsen memory for recent events, leading to functional deficits (Tromp D, Duour A, Lithfous S, Pebayle T, Despres O. "Episodic memory in normal ageing and Alzheimer disease: Insights from imaging and behavioral studies." Ageing Res Rev. (2015); 24:232-62).

Episodic memory can be assessed by clinical tests such the Wechsler Memory Scale (WMS) or Hopkins Verbal Learning Test—Revised (HVLT-R). In clinical practice, episodic memory may also be assessed by components of the Mini-Mental State Examination (MMSE).

The WMS is a neuropsychological test designed to measure different memory functions in a human subject. The current version of this test, the WMS-IV is made up of seven subtests: Spatial Addition, Symbol Span, Design Memory, General Cognitive Screener, Logical Memory(I & II), Verbal Paired Associates(I & II), and Visual Reproduction(I & II). A person's performance is reported as five Index Scores: Auditory Memory, Visual Memory, Visual Working Memory, Immediate Memory, and Delayed Memory. The latter two Index scores (i.e Immediate and Delayed Memory, respectively) specifically assess episodic memory.

The HVLT-R is a measure of verbal episodic memory that consists of 3 initial learning trials, a delayed recall trial and a yes/no delayed recognition trial. The HVLT-R comes in 6 alternative and parallel forms, thereby reducing the potential of a practice effect.

The MMSE is a brief evaluation of orientation, registration, attention, recall, language, and constructional praxis. The MMSE is highly reproducible and is a useful tool for evaluating the mental state and abilities of human patients. In addition to its value in screening patients for dementia or patients at risk for dementia, the MMSE is often used to document cognitive decline over time in individual patients. (Clark, C. M. et al., "Variability in annual Mini-Mental State Examination score in patients with probable Alzheimer disease; a clinical perspective of data from the Consortium to Establish a Registry for Alzheimer's Disease," Arch Neurol. July; 56(7):857-62 (4999)).

SUMMARY

The present disclosure encompasses the surprising discovery that treatment with VX-745 can improve mental function, such as episodic memory, in a subject suffering from or at risk for developing dementia relative to baseline mental function assessed prior to treatment.

In the case of most progressive dementias, including Alzheimer's disease, there is no cure, nor is there any treatment that slows, stops, or reverses its progression. As a result, there is along-felt need for treatments for dementia, particularly dementia associated with Alzheimer's disease. In particular, there is a need for disease modifying drugs capable of slowing the rate of decline and improving mental state and function, as assessed by clinical scales, in patients suffering from or susceptible to dementia, particularly dementia associated with Alzheimer's disease.

As disclosed herein, in clinical studies, human subjects treated with VX-745 were surprisingly found to have improvements in episodic memory. In a 12-week clinical study, human subjects treated with VX-745 demonstrated improvement in episodic memory as assessed by the WMS Immediate and Delayed Recall. In a 6 week clinical study, human subjects treated with VX-745 demonstrated improvements in episodic memory as assessed by the HVLT-R.

The MMSE was utilized to assess patients for mild cognitive impairment (MCI), or early signs of dementia that may be associated with Alzheimer's disease, as well as episodic memory. The MMSE was performed on more than one occasion during the study to ascertain that treatment with VX-745 would not adversely affect the mental status or function of patients, as well as to monitor whether there was a reduction in the rate of cognitive decline of the human study subjects. In both a 6-week 12-week clinical study patients surprisingly showed improvement in MMSE scores as compared to baseline. Those of skill in the art have previously thought that reversal of dementia, particularly dementia associated with neurodegenerative disease, may not be possible, particularly by a monotherapy. (Lawrence, J., "Alzheimer's will be treated with 'cocktail' of drugs, predicts neuroscientist," The Pharmaceutical journal, Vol. 296 No. 7885 (online) (2016)).

In some embodiments, the invention provides methods of improving episodic memory in a human subject; the methods comprising administering to the subject a therapeutically effective amount of VX-745.

In some embodiments, a human subject has dementia.

In some embodiments, a human subject is predisposed to dementia.

In some embodiments, a human subject has mild cognitive impairment (MCI).

In some embodiments, a human subject has a neurodegenerative disorder.

In some embodiments, the invention provides methods of treating dementia in a human subject exhibiting a decline in at least one of the following: memory; communication and language; ability to focus and pay attention; reasoning and judgment; and visual perception; the methods comprising administering to the subject a therapeutically effective amount of VX-745.

In some embodiments, the invention provides methods for treating subjects susceptible to or at risk of developing or progressing to dementia. In some embodiments, the human subject has Alzheimer's disease. In some embodiments, the human subject has mild cognitive impairment.

In some embodiments, the invention provides methods of treating dementia in a human subject exhibiting a decline in at least two of the following: memory; communication and language; ability to focus and pay attention; reasoning and judgment; and visual perception; the methods comprising administering to the subject a therapeutically effective amount of VX-745.

In some embodiments, the treating results in one or more of complete or partial reversal of existing memory deficits, improvement in memory function (e.g., episodic memory function), and a decrease in the rate of decline of memory function. In some embodiments, the treatment results in both a decrease in the rate of decline of memory function and improvement in memory function.

In some embodiments, a therapeutically effective amount of VX-745 provides an average blood concentration from about 1 ng/mL, to about 15 ng/mL, from about 1 ng/mL to about 10 ng/mL, from about 5 ng/mL to about 15 ng/mL, or from about 5 ng/mL to about 10 ng/mL. In some embodiments, blood concentration is about 8 ng/mL.

In some embodiments, a therapeutically effective amount is achieved by twice daily administration. In some embodiments, twice daily administering occurs about 9 to 15 hours apart. In some embodiments, twice daily administering occurs about 12 hrs apart. In some embodiments, administering occurs within about 30 to 60 minutes after a subject consumes food.

In some embodiments, VX-745 is administered at a dose of from about 40 mg to about 125 mg. In some embodiments, VX-745 is administered at a dose of 40 mg.

In some embodiments, a therapeutically effective amount of VX-745 is from about 80 mg to about 500 mg per day. In some embodiments, a therapeutically effective amount of VX-745 is from about 80 mg to about 250 mg per day. In some embodiments, a therapeutically effective amount is about 80 mg per day.

In some embodiments, VX-745 is in the form of a pharmaceutically acceptable composition.

In some embodiments, VX-745 is administered to a human subject that has a baseline mini mental state examination score from about 20 to about 28 prior to treatment.

In some embodiments, treating of a human subject results in at least a 3 point increase over the baseline mini mental state examination score. In some embodiments, treating of a human subject results in maintaining a baseline mini mental examination score. In some embodiments, administration of VX-745 to a human subject results in an improvement in one or more of: memory; communication and language; ability to focus and pay attention; reasoning and judgment; and visual perception. In some embodiments, administration of VX-745 to a human subject results in an improvement in two or more of: memory; communication and language; ability to focus and pay attention; reasoning and judgment; and visual perception. In some embodiments, administration of VX-745 to a human subject results in an improvement in mental status and function.

In some embodiments, methods are provided for administrating VX-745 to modify pathophysiology associated with dementia and improve one or more of: memory; communication and language; ability to focus and pay attention; reasoning and judgment; and visual perception.

In some embodiments, methods are provided for administering VX-745 to modify pathophysiology associated with dementia and reverse existing memory deficits. In some embodiments, methods are provided for administering VX-745 to modify pathophysiology associated with dementia and improve memory function. In some embodiments, methods are provided for administering VX-745 to modify pathophysiology associated with dementia and slow decline in memory function. In some embodiments, methods are provided for administering VX-745 to modify pathophysiology associated with dementia and slow decline in and improve memory function.

In some embodiments, methods are provided for administrating VX-745 to modify pathophysiology associated with Alzheimer's disease and improve one or more of: memory; communication and language; ability to focus and pay attention; reasoning and judgment; and visual perception.

In some embodiments, methods are provided for administering VX-745 to modify pathophysiology associated with Alzheimer's disease and reverse existing memory deficits. In some embodiments, methods are provided for administering VX-745 to modify pathophysiology associated with Alzheimer's disease and improve memory function. In some embodiments, methods are provided for administering VX-745 to modify pathophysiology associated with Alzheimer's disease and slow decline in memory function. In some embodiments, methods are provided for administering VX-745 to modify pathophysiology associated with Alzheimer's disease and slow decline in and improve memory function.

In some embodiments, improvements are measurable by Mini Mental State Examination scoring. In some embodiments, improvements are measurable by Wechsler Memory Scale (WMS) scoring. In some embodiments, improvements are measurable by Hopkins Verbal Learning Test-Revised (HVLT-R) scoring. In some embodiments, improvements are measurable by Clinical Dementia Rating (CDR) scoring. In some embodiments, improvements are measurable by Columbia Suicide Severity Rating Scale (C-SSRS) scoring. In some embodiments, improvements are measurable by Alzheimer's Disease Assessment Scale-Cognitive (ADAS-Cog) scoring. In some embodiments, improvements are measurable by Alzheimer's Disease Cooperative Study—Clinical Global Impression of Change (ADCS-CGIC) scoring. In some embodiments, improvements are measurable by Alzheimer's Disease Cooperative Study—Activities of Daily Living 19-item (ADCS-ADL19) scoring. In some embodiments, improvements are measurable by Alzheimer's Disease Cooperative Study—Activities of Daily Living 23-item (ADCS-ADL23) scoring.

In some embodiments, improvements are measurable by neuropsychological testing. In some embodiments, improvements are measurable by radiological testing. In some embodiments, improvements are measurable by evaluation of cerebrospinal fluid (CSF). In some embodiments, improvements are measurable by neuroimaging. In some embodiments, improvements are measurable by one or more of magnetoencephalography (MEG), electroencephalogram (EEG), and/or functional magnetic resonance imaging (fMRI).

In some embodiments, VX-745 is administered orally. In some embodiments, VX-745 is administered parenterally.

In some embodiments, the invention provides compositions comprising VX-745 for use in treating dementia in a human subject. In some embodiments, a subject exhibits a decline in at least one, or at least two, of the following: memory (e.g., episodic memory); communication and language; ability to focus and pay attention; reasoning and judgment; and visual perception.

In some embodiments, the composition for use comprises an amount of VX-745 from about 40 mg to about 125 mg. In some embodiments, the amount of VX-745 is 40 mg.

In some embodiments, the composition for use is administered twice daily. In some embodiments, the composition for use is formulated for oral delivery.

In some embodiments, the invention provides compositions for use in the manufacture of a medicament for use in a method of treating dementia.

BRIEF DESCRIPTION OF DRAWINGS

FIG. 1 depicts exemplary mini mental state examination (MMSE) parameters used to assess patients to determine level of mental function.

FIG. 4 shows the patient demographic in a study to evaluate VX-745 effects on endpoints including amyloid plaque load, PK/PD, safety and tolerability, and synaptic function. Patients were randomly assigned to one of the two VX-745 dose groups and administered either 40 mg or 125 mg of VX-745, twice daily for 12 weeks.

FIG. 5 shows incidence of adverse events. VX-745 (40 mg or 125 mg) was administered twice daily for 12 weeks.

FIG. 10 shows the patient demographic in a study to evaluate VX-745 effects on endpoints including pharmacodynamic activity of VX-745 in the central nervous system of patients with MCI due to AD or with mild AD. Patients were administered either 40 mg or 125 mg of VX-745, twice daily for 6 weeks. Other objectives included evaluation of safety and tolerability, as well as plasma and CSF PK profile.

DEFINITIONS

Figure 2:
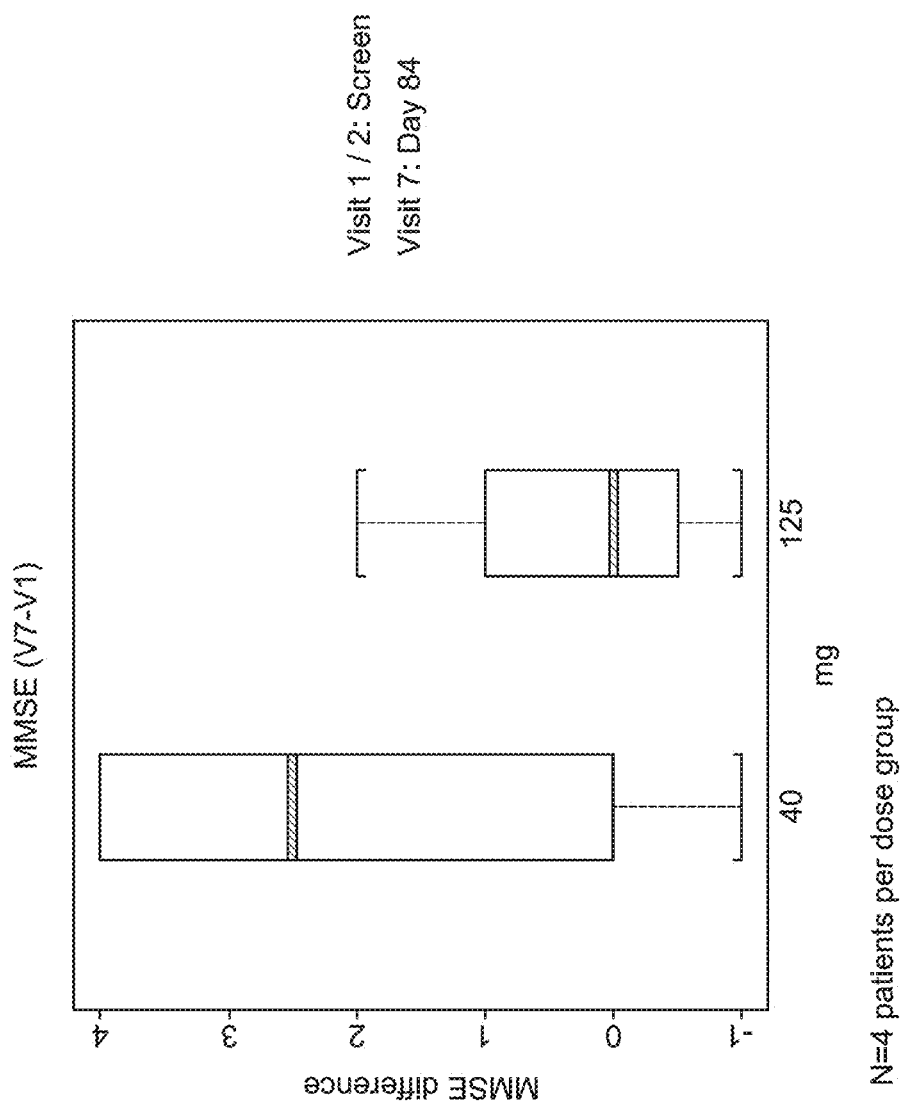
FIG. 2 depicts an exemplary graph of absolute change in MMSE scores of four patients, treated with either 40 mg or 125 mg VX-745.

Carrier: The, term "carrier" refers to any chemical entity that can be incorporated into a composition containing an active agent (e.g., a p38 MAPKα inhibitor such as VX-745) without significantly interfering with the stability and/or activity of the agent (e.g., with a biological activity of the agent). In certain embodiments, the term "carrier" refers to a pharmaceutically acceptable carrier. An exemplary carrier herein is water.

Combination. As used herein, the term "combination," "combined," and related terms refers to a subject's simultaneous exposure to two or more therapeutic agents in accordance with this invention. For example, an agent (p38 MAPKα inhibitor such as VX-745) may be administered with another therapeutic agent simultaneously or sequentially in separate unit dosage forms or together in a single unit dosage form. Accordingly, the present invention provides, among other things, dosing regimens that involve administering at least an agent of the present invention (p38 MAPKα inhibitor such as VX-745), an additional therapeutic agent, and a pharmaceutically acceptable carrier, adjuvant, or vehicle (the pharmaceutically acceptable carrier, adjuvant, or vehicle typically being in association with one or both of the VX-745 and the additional therapeutic agent).

Dementia. The term "dementia" as used herein refers to a decline in one or more of the following mental functions; memory; communication and language; ability to focus and pay attention; reasoning and judgment; and visual perception. In some embodiments, dementia is associated with Alzheimer's disease.

Formulation. The term "formulation" as used herein refers to a composition that includes at least one active agent (e.g., p38 MAPKα inhibitor such as VX-745) together with one or more carriers, excipients or other pharmaceutical additives for administration to a patient. In general, particular carriers, excipients and/or other pharmaceutical additives are selected in accordance with knowledge in the art to achieve a desired stability, release, distribution and/or activity of active agent(s) and which are appropriate for the particular route of administration.

Neuroimaging. As used herein, the term "neuroimaging" refers to a technique which directly or indirectly images the structure or function of the brain. In some embodiments, the term "neuroimaging" refers to a technique selected from computerized axial tomography (CAT or CT), single photon emission computed tomography (SPECT), positron emission, tomography (PET), magnetic resonance imaging (MRI) or functional magnetic resonance imaging (fMRI). In some embodiments, a neuroimaging technique employs one or more imaging agents such as radioactive, fluorescent or other detectable ligands. In some embodiments, a fluorescent ligand is Pittsburg compound B ([N-Methyl-$^{11}$C]$_2$-(4'-methylaminophenyl)-6-hydroxybenzothiazole), a fluorescent analog of thioflavin T. In some embodiments, a radioactive ligand is Amyvid® (florbetapir $^{18}$F) or $^{18}$F-flutemetamol. In some embodiments, the neuroimaging technique is PET scan using Pittsburgh compound B as an imaging agent. In some embodiments, the neuroimaging technique is PET scan using Amyvid® as an imaging agent. In some embodiments, the neruoimaging technique is PET scan using $^{18}$F-flutemetamol as an imaging agent.

Neuroimage. As used herein, the term "neuroimage" refers to an image or picture generated by a neuroimaging technique. In some embodiments, a "neuroimage" refers to one or more of CAT (or CT), SPECT, PET, MRI or fMRI scans.

Parenteral. The term "perenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. The suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Patient. The "patient" as used herein means a human to which a formulation or composition comprising a formulation is administered.

Pharmaceutically acceptable carrier, adjuvant, or vehicle. The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Therapeutic agent. As used herein, the phrase "therapeutic agent" refers to any agent that elicits a desired biological or pharmacological effect when administered to a subject.

Therapeutically effective amount and effective amount. As used herein, and unless otherwise specified, the "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence and/or magnitude of) one or more symptoms associated with the disease, disorder or condition to be treated. In some embodiments, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition.

Treat or Treating. The terms "treat" or "treating," as used herein, refer to partially or completely alleviating, inhibiting, delaying onset of, reducing the incidence of, yielding prophylaxis of, ameliorating and/or relieving or reversing a disorder, disease, or condition, or one or more symptoms or manifestations of the disorder, disease or condition.

Unit Dose. The expression "unit dose" as used herein refers to a physically discrete unit of a formulation appropriate for a subject to be treated (e.g., for a single dose); each unit containing a predetermined quantity of an active agent selected to produce a desired therapeutic effect when administered according to a therapeutic regimen (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form (e.g., a tablet or capsule), a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present invention will be decided by the attending physician within the scope of sound medical judgment. The specific effective dose level for any particular subject may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment drugs and/or additional therapies used in combination or coincidental with specific compound(s) employed, and like factors well known in the medical arts. In some embodiments, a unit dose of a p38 MAPKα inhibitor, such as VX-745 is about 1 mg, 3 mg, 5 mg, 10 mg. 15 mg, 20 mg, 25 mg, 30 mg, 35 mg, 40 mg, 45 mg, 50 mg, 100 mg, 125 mg, or 50 mg.

DETAILED DESCRIPTION OF CERTAIN EMBODIMENTS

Treatment for patients suffering from, or at risk of, dementia, particularly dementia associated with Alzheimer's disease, is limited. Physicians urgently need new strategies for treatment of dementia.

The present invention provides, among other things, compositions and methods for treating dementia and/or dementia associated with Alzheimer's disease in a subject. In particular, the present invention provides methods for promoting recovery of function in a subject suffering from dementia and/or dementia associated with Alzheimer's disease, by administering a composition comprising the selective p38 MAPKα inhibitor VX-745. In some embodiments, the invention provides methods for treating dementia by administering a composition comprising the selective p38 MAPKα inhibitor VX-745.

In some embodiments, the invention provides compositions and methods for treating subjects susceptible or at risk of development or progression of dementia.

Various aspects of the invention are described in detail in the following sections. The use of sections is not meant to limit the invention. Each section can apply to any aspect of the invention. In this application, the use of "or" means "and/or" unless stated otherwise.

Dementia

Dementia is a category of brain disease which is characterized by a long term, often gradual, decrease in a person's memory or other thinking skills that is great enough to affect daily functioning. Common causes of dementia include Alzheimer's disease, vascular dementia, Lewy body dementia and frontotemporal dementia. A person may suffer from more than one type of dementia.

Synaptic loss occurs early neurodegenerative protein misfolding diseases. These include, but are not limited to, Alzheimer's and Parkinson's diseases, Lewy Body Dementia, frontotemporal dementia, the tauopathies, amyotrophic lateral sclerosis, and prion diseases. Each of these disorders has a characteristic clinicopathological profile associated with the accumulation of disease-specific misfolded protein in the brain and central nervous system. Freeman, O. J. & Mallucci, G. R., "The UPR and synaptic dysfunction in neurodegeneration," *Brain Research,* 1648 (Part B): 530-537(2016).

Synaptic dysfunction is associated with impairment of memory (e.g., episodic memory), mental status, and/or mental function. During disease progression, increasing synaptic dysfunction and loss leads eventually to neuronal cell death. Synaptic function may be assessed and monitored by methodologies including, but not limited to, magnetoencephalography (MEG), electroencephalogram (EEG), and/or functional magnetic resonance imaging(fMRI).

Mechanistically, disruption of protein trafficking inside neurons may be a pathogenic event, and possibly a common pathophysiologic event, that underlies the development of memory deficits and other cognitive deficits in Alzheimer's disease and other dementias. Such physiologic defects may involve alterations of lysosomal function, including autophagy-lysosomal mediated protein degradation and endolysosomal (endocytosis) mediated protein receptor turnover (Perik, A. & Annaert, W., "Early etiology of Alzheimer's disease: tipping the balance toward autophagy or endosomal dysfunction?," *Acta Neuropathol* 129:363-381 (2015); Nixon, R. A., "The role of autophagy in neurodegenerative disease." *Nat Medicine* 19:983-997 (2013); Nixon, R. A. & Yang, D. S., "Autophagy failure in Alzheimer's disease—locating the primary defect," *Neurobiol Dis* 43(1): 38-45 (2011); Funk, K. E. & Kuret, J., "Lysosomal Fusion Dysfunction as a Unifying Hypothesis for Alzheimer's Disease Pathology," *Int J of Alzheimer's Dis* (2012); Zhang, L., Sheng, R., Qin, Z., "The lysosome and neurodegenerative diseases," *Acta Biochim Biphys Sin* 437-445 (2009); Sannerud, R. & Annaert, W., "Bin1 and CD2AP polarize Ab generation in neurons," *EMBO Rep* 18:5-7 (2017)). As an example, Familial Alzheimer's disease (FAD) demonstrates a connection between abnormalities in lysosomal function and the development of synaptic dysfunction and cognitive deficits. Expression of FAD-associated genes in vitro leads to endolysosomal dysfunction and in transgenic animal models with endosomal abnormalities (specifically accumulation of early and enlarged endosomes) associated with synaptic dysfunction, both of which precede accumulation of amyloid plaque. Studies on human autopsy-derived brain with Alzheimer's disease indicate that endosomal abnormalities may be one of the earliest pathologic events in the disease. Many of the major late onset Alzheimer's disease associated genes (e.g. Apoe4, Bin1) have been linked to disruption of endosomal function.

While symptoms can vary greatly, a diagnosis of dementia or dementia associated with Alzheimer's disease may be made when at least two of the following core mental functions are significantly impaired: memory, communication and language, ability to focus and pay attention, reasoning and judgment, and visual perception.

Types of memory systems include: episodic memory, semantic memory, simple classical conditioning, procedural memory, working memory, and priming (Gold, C. A. and Budson, A. E, "Memory loss in Alzheimer's disease: implications for development of therapeutics," Expert Rev. Neurother. 8(12):1879-91 (2008)). Each of these types of memory systems may be differentially affected depending on the disease. Episodic memory, semantic memory, classical conditioning, working memory, and/or priming may be disrupted in patients with Alzheimer's disease. Impairment of episodic memory is one of the earliest signs and symptoms of Alzheimer's disease.

Brain regions associated with episodic memory include the medial temporal lobes, especially the hippocampus; the anterior and dorsomedial nuclei of the thalamus; the fornix; the mammillary bodies; the mammillothalamic tract and the retrosplenial cortex (Gold, C. A. and Budson, A. E. "Memory loss in Alzheimer's disease: implications for development of therapeutics," Expert Rev. Neurother. 8(12): 1879-91 (2008)). Other brain structures may also function in episodic memory, including the diagonal band of Broca's area and the presubiculum.

Impairment of episodic memory can be associated with dementia or dementia associated with Alzheimer's disease. Episodic memory is used to record, store/consolidate, and retrieve information about personal experiences and the temporal and spatial contexts of those experiences (Tromp, D. et al., "Episodic memory in normal aging and Alzheimer disease: Insights from imaging and behavioral studies," *Ageing Res. Rev.* (2015)). Episodic memory includes autobiographical recollection and verbal or non-verbal laboratory tasks involving recognition or recall (e.g., a list of words). Several brain systems are thought to be involved in episodic memory recording and retrieval, including the frontal system and temporal hippocampal system, as well as other structures, such as the parietal cortex, cerebellum, thalamus, and cingulate gyrus. Various changes in the nervous system may be related to decline in episodic memory, including: morphological brain changes (e.g., alterations in the prefrontal cortex brain region, which is associated with executive function); decrease in white and gray matter volumes, neuronal numbers and size; reduced efficiency of synaptic contacts and decreases in the concentrations or signaling of neurotransmitters (e.g. dopamine, acetylcholine). Episodic memory decline may also result from degradation of cognitive resources, such as speed processing, inhibitory function and attentional resources.

Dementia and/or Alzheimer's disease may be diagnosed and monitored using one or more of the Mini-Mental State Examination (MMSE), Wechsler Memory Scale (WMS), the Hopkins Verbal Learning Test-Revised (HVLT-R), Clinical Dementia Rating (CDR), the Columbia Suicide Severity Rating Scale (C-SSRS), Alzheimer's Disease Assessment Scale-Cognitive (ADAS-Cog), neuropsychological testing, radiological testing, evaluation of cerebrospinal fluid (CSF), and neuroimaging.

Brain modifications related to episodic memory decline have been studied by functional neuroimaging techniques, such as functional Magnetic Resonance Imaging (fMRI) and Positron Emission Tomography (PET). Cognitive aging studies and neurobiological studies have characterized the effects of aging on behavioral performance and effects on the brain, respectively. In vivo neuroimaging techniques may be used to characterize the brain in action and examine the links between behavior and function.

Episodic memory may be tested verbally or non-verbally. Tests of experimental episodic memory encoding include verbal material (words), non-verbal material (pictures, scenes, objects, music, etc.), and the context under which the episodic memory was acquired (e.g., source of the experience and contextual details). In an example of episodic memory test, an individual is tested to determine if they can associate the episodic memory (e.g., a word from a list) with particular details (e.g., emotion, time place, etc.). Neuroimaging techniques allow the study of the neuroanatomical bases of the encoding process. Storage/consolidation of episodic memory can be measured by delayed recall in time of the previously recorded information (encoding) and after an interfering activity.

Various tests can also be used to measure episodic memory retrieval. In free recall, a list of items is presented to remember during encoding (e.g., words, sounds or pictures) and the subject is asked to recall as many items as possible in any order following a delay of variable duration. Number of items correctly recalled and number of mistakenly recalled items (e.g., words that were not studied), are measured. In cued recall, a list of items to remember is presented during encoding and is then tested with cues aimed at helping a subject remember the material.

Episodic memory can be evaluated by measures of recall and recognition. Assessment of episodic memory and learning can be performed by providing specific verbal or visual information to a test subject and asking the subject to either immediately provide the information back ("immediate recall") or after a lag of 20 to 30 minutes ("delayed recall").

Symptomatic therapies have thus far failed to demonstrate positive effects on episodic memory, as they appear to primarily act by increasing attention, rather than impacting underlying synaptic dysfunction.

There is a large population of human patients susceptible to dementia, at risk of developing dementia, or are suffering from dementia, particularly dementia associated with Alzheimer's disease. Some patients have mild cognitive impairment (MCI), sometimes referred to as "pre-dementia," with or without having detectable plaques, tangles, or other hallmark pathologies of Alzheimer's disease. There is also a clinically significant percentage of patients clinically diagnosed with Alzheimer's disease that do not display β-amyloid accumulation even though neurodegeneration is in progress. (Castello, M. A., et al., "Moving beyond anti-amyloid therapy for the prevention and treatment of Alzheimer's disease," *BMC Neurology* 14:169 (2014)).

In some embodiments, patients may be diagnosed with susceptibility to dementia, at risk of development of dementia, dementia, and/or MCI (e.g., pre-dementia), and monitored using one or more of the mini-mental state examination (MMSE), Wechsler Memory Scale (WMS), the Hopkins Verbal Learning Test-Revised (HVLT-R), Clinical Dementia Rating (CDR), the Columbia Suicide Severity Rating Scale (C-SSRS), Alzheimer's Disease Assessment Scale-Cognitive (ADAS-Cog), neuropsychological testing, radiological testing, and neuroimaging.

In some embodiments, the present invention provides a method of stabilizing or improving one or more of: memory (e.g., episodic memory), communication and language, ability to focus and pay attention, reasoning and judgment, and visual perception. In some embodiments, the present invention provides a method of stabilizing or improving at least two of: memory, communication and language, ability to focus and pay attention, reasoning and judgment, and visual perception.

The MMSE is a questionnaire used extensively in clinical and research settings to measure mental function. It is commonly used to screen for dementia, and to assess the severity and progression of dementia. The MMSE is an effective way to document a human subject's response to treatment. The test examines functions including registration, attention and calculation, recall, language, ability to follow simple commands and orientation. Exemplary mini-mental state examination parameters are provided in FIG. 1.

The WMS is a neuropsychological test designed to measure different memory functions in a human subject. The current version of this test, the WMS-IV is made up of seven subtests: Spatial Addition, Symbol Span, Design Memory, General Cognitive Screener, Logical Memory(I & II), Verbal Paired Associates(I & II), and Visual Reproduction(I & II). A person's performance is reported as five Index Scores: Auditory Memory, Visual Memory, Visual Working Memory, immediate Memory (Recall), and Delayed Memory (Recall). Immediate Recall and Delayed Recall Index scores reflect episodic memory function.

The Hopkins Verbal Learning Test-Revised (HVLT-R) is a measure of verbal episodic memory that consists of 3 initial learning trials, a delayed recall trial and a yes/no delayed recognition trial. The HVLT-R comes in 6 alternative and parallel forms, thereby reducing the potential of a practice effect.

The Clinical Dementia Rating (CDR) measures dementia severity by examining 6 domains: Memory, Orientation, Judgment and Problem-Solving, Community Affairs, Home and Hobbies, and Personal Care. Informants are administered a structured interview, to collect information about the participants daily life in these 6 areas. Scoring is done on, 3 point scale for each of the 6 domains and an overall box score is obtained assessing overall, dementia severity (sum of box, SOB).

The Columbia Suicide Severity Rating Scale (C-SSRS) is a questionnaire for suicide assessment that can be used for subjects with dementia.

Alzheimer's Disease

Alzheimer's disease is a leading cause of dementia, Alzheimer's disease pathology is characterized by the deposition of extracellular amyloid plaques in the brain parenchyma and neurofibrillary tangles within neurons, along with neuronal and synaptic loss.

Age and APOE4 genotype are the two greatest risk factors for Alzheimer's disease. As many as six cognitive domains are affected in individuals with Alzheimer's disease: memory, executive functioning, language, visuospatial functioning, attention and affect.

Mild cognitive impairment (MCI) is a preclinical period of Alzheimer's Disease, during which early and mild cognitive deficits can be recognized. In approximately 50% of individuals with MCI, Alzheimer's Disease pathology can evolve within a few years. Deficits in episodic memory, including disorders of encoding and storage, appear in the very early stages (e.g. MCI) of Alzheimer's Disease. During the course of progression to Alzheimer's Disease, affected brain regions also progress. In the first stages of the disease (i.e., MCI), the entorhinal cortex and associated structures in the anterior medial temporal lobe (MTL) are affected, with AD lesions progressing to the parietal cortex and neocortex, and then the frontal lobe.

There is currently no therapy available for Alzheimer's disease that reverses and/or slows disease progression. Synaptic dysfunction has emerged as an important therapeutic objective for AD disease modification. Therapeutic interventions that target synaptic dysfunction have the potential to both reverse existing functional deficits and slow further decline.

Synaptic dysfunction in the brain region responsible for memory formation (the hippocampus) is a pathogenic event that underlies the development of AD-related memory disorders (Gallagher, M. & Koh, M. T, "Episodic Memory on the Path to Alzheimer's Disease," Curr. Opin. Neurobiol. 21(6): 929-934 (2011); Gold, C. A., & Budson, A. E., "Memory loss in Alzheimer's disease: implications for development of therapeutics." *Expert Rev Neurother.* 8(12): 1879-1891 (2008)), which manifests itself as disruption in a very specific hippocampal-dependent function called "episodic memory".

Acetylcholinesterase inhibitors are currently prescribed for treatment of the cognitive impairments in Alzheimer's disease. These inhibitors may improve cognitive functioning by increasing neurotransmitter concentration at cholinergic synapses. Examples of acetylcholinesterase inhibitors include donepezil, galantamine, rivastigmine and tacrine.

Other therapies for Alzheimer's disease may include memantine, a NMDA receptor antagonist, and monoclonal antibodies or antibody fragments against Aβ.

VX-745

Many extracellular stimuli including pro-inflammatory cytokines and other inflammatory mediators, elicit specific cellular responses through the activation of mitogen-activated protein kinase (MAPK) signaling pathways. MAPKs are proline-targeted serine-threonine kinases that transduce environmental stimuli to the nucleus. Once activated, MAPKs other kinases or nuclear proteins through phosphorylation, including potential transcription factors and substrates. The four isoforms (α, β, δ, and γ) of p38 MAP kinase comprise one specific family of MAPKs that mediate responses to cellular stresses inflammatory signals.

The role of p38 MAPK in the various stages of inflammation has prompted the discovery of several compounds capable of inhibiting p38 (SB203580, RWJ 67657, L-167307, VX-745, RPR200765A and others). (See, e.g., Kumar et al., "p38 MAP Kinases: Key Signaling Molecules as Therapeutic Targets for Inflammatory Diseases," *Nature Reviews,* 2:717-726 (2003); Brown et al., "p38 MAP kinase inhibitors as potential therapeutics for the treatment of joint degeneration and pain associated with osteoarthritis," *J. Inflammation* 5:22 (2008)). These pharmacological inhibitors are cytokine-suppressive anti-inflammatory drugs responsible for in vitro and in vivo inhibition of lipopolysaccharide-induced tumor necrosis factor-α (TNF-α) production, and have been developed in accordance with the primary pharmacologic action presumed to being reduction of inflammation; for example, in clinical studies doses were administered to achieve blood concentrations that met or exceeded the whole blood IC50 (inhibitory concentration for 50% maximal effect) for inhibition of cytokine (IL-1β or TNFα).

Figure 3:
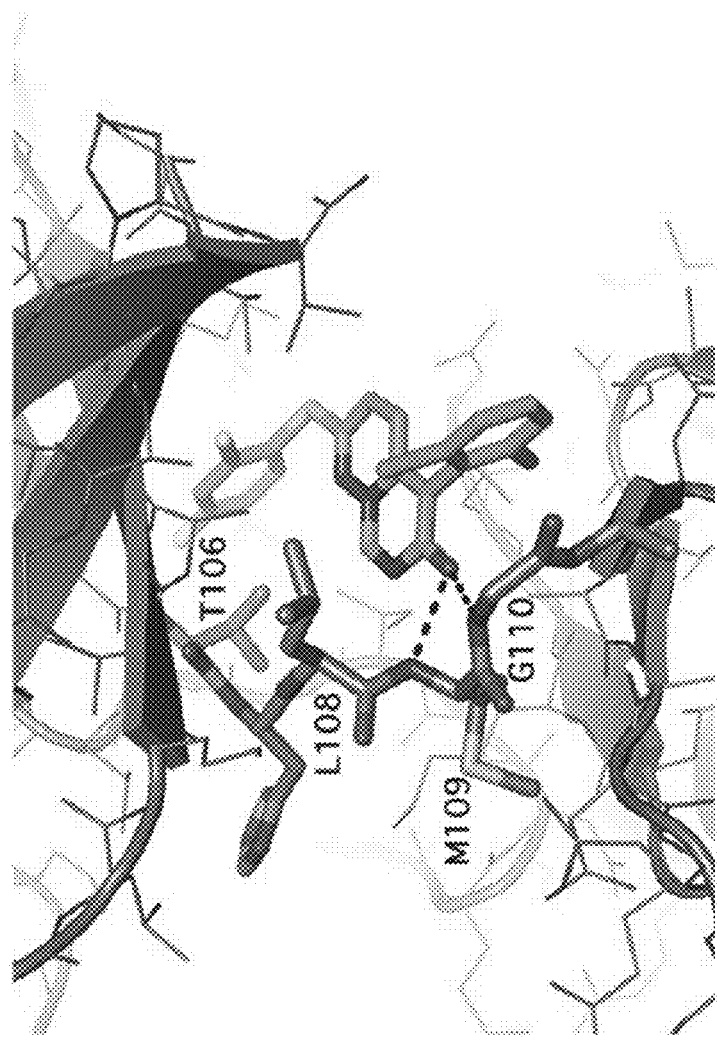
FIG. 3 depicts the crystal structure of VX-745 bound to p38 MAPKα.

VX-745 is a selective small-molecule inhibitor of the alpha isoform of p38 MAPK, previously developed by Vertex Pharmaceuticals for the treatment of rheumatoid arthritis (RA). FIG. 3 depicts the crystal structure of VX-745 bound to p38 MAPKα.

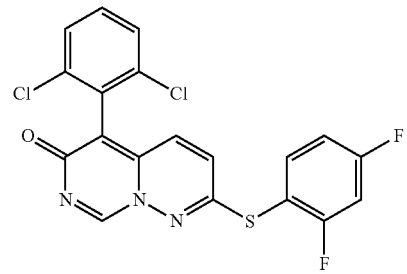

VX-745

Without wishing to be bound by theory, it is believed that the clinical failures of p38 MAPKα inhibitors to treat chronic inflammatory conditions such as rheumatoid arthritis are due to redundancy of the inflammatory (cytokine production) pathways. Such redundancy results in the upregulation of feedback loops when p38 MAPK-mediated cytokine production is chronically inhibited, leading to an overall lack of efficacy.

Without wishing to be bound by theory, as indicated by Example 4, it is believed that VX-745 may act to improve episodic memory by reversing impaired endolysosomal function within neurons that leads to synaptic dysfunction within the hippocampus, a region of the brain responsible for proper episodic memory function.

Methods

In certain embodiments, a provided method comprises administering to a human subject in need thereof VX -745, or a pharmaceutically acceptable composition thereof, at a dose providing an average blood concentration from about 1 to about 15 ng/mL. In some embodiments, the human subject in need thereof is suffering from dementia. In some embodiments, the human subject is suffering from dementia associated with Alzheimer's disease. In some embodiments, a provided method comprises administering to a human subject in need thereof a dose of VX-745, or a pharmaceutically acceptable composition thereof, providing an average blood concentration of from about 1 ng/mL to about 15 ng/mL, from about 1 ng/mL to about 10 ng/mL, from about 5 ng/mL to about 15 ng/mL, or from about 5 ng/mL to about 10 ng/mL.

In some embodiments, a provided method comprises administering to a human subject in need thereof a dose of VX-745, or a pharmaceutically acceptable composition thereof, providing an average blood concentration of 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, or 15 ng/mL.

In some embodiments, a provided method comprises administering to a human in need thereof a dose of VX-745, or a pharmaceutically acceptable composition thereof, providing an average blood concentration of about 8 ng/mL.

In certain embodiments, the present invention provides a method of treating dementia in a human subject comprising administering to human subject exhibiting a decline in at least two of the following: memory; communication and language; ability to focus and pay attention; reasoning and judgment; and visual perception; a dose of VX-745, or a pharmaceutically acceptable composition thereof, providing an average blood concentration about 1 ng/mL to about 15 ng/mL, from about 1 ng/mL to about 10 ng/mL, from about 5 ng/mL to about 15 ng/mL, or from about 5 ng/mL to about 10 ng/mL.

Pharmaceutical Compositions

In some embodiments, a provided method comprises administering to a patient a pharmaceutical composition comprising NIX-745 together with one or more therapeutic agents and a pharmaceutically acceptable carrier, adjuvant, or vehicle. In some embodiments, the present invention provides a pharmaceutical composition comprising a dose of VX-745 together with one or more therapeutic agents and a pharmaceutically acceptable carrier, adjuvant, or vehicle, wherein the dose of VX-745 results in an average blood concentration of from about 1 ng/mL to about 15 ng/mL, from about 1 ng/mL to about 10 ng/mL, from about 5 ng/mL to about 15 ng/mL, or from about 5 ng/mL to about 10 ng/mL.

In some embodiments, the present invention provides a pharmaceutical composition comprising a dose of VX-745 together with one or more therapeutic agents and a pharmaceutically acceptable carrier, adjuvant, or vehicle, wherein the dose of VX-745 results in an average blood concentration of about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, or 15 ng/mL.

In certain embodiments, pharmaceutically acceptable compositions of this invention are formulated for oral administration. Pharmaceutically acceptable compositions of this invention may be orally administered in any orally acceptable dosage form including, but not limited to, capsules, caplets, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

The quantities of the compounds of the present invention that are combined with the carrier materials to produce a composition in a single dosage form will vary depending upon the patient and the particular mode of administration. Preferably, provided compositions should be formulated so that a dosage of between 1-500 mg/day of VX-745 can be administered to a patient receiving these compositions. Examples of compositions include compositions formulated to administer dosages of between 1-10 mg, 10-25 mg or 25-50 mg or 125-250 mg of VX-745 to the patient receiving these compositions. In some embodiments, the composition is formulated into doses containing 1 mg, 3 mg, 5 mg, 10 mg, 20 mg, 25 mg, 30 mg, 40 mg, 50 mg, 80 mg, 100 mg, 125 mg, or 250 mg of the active composition. Dosing regimens for these formulations may include but are not limited to single administration dosing, once, twice, or three times daily dosing, weekly dosing, and monthly dosing. In some embodiments, a provided composition is formulated to provide 40 mg/dose of VX-745. In some embodiments, a provided composition is formulated to provide 80 mg/dose of VX-745. In some embodiments, a provided composition is formulated to provide 100 mg/dose of VX-745. In some embodiments, a provided composition is formulated to provide 125 mg/dose of VX-745. In some embodiments, a provided composition is formulated to provide 250 mg/dose of VX-745. In some embodiments, a provided composition is formulated to provide 80 mg/day of VFX-745. In some embodiments, a provided composition is formulated to provide 250 mg/day of VX-745.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Dosing

In some embodiments, a compositions are administered in a therapeutically effective amount and/or according to a dosing regimen that is correlated with a particular desired outcome (e.g., with treating or reducing risk for disease).

Any provided composition as described herein may be administered by any appropriate route. In some embodiments, provided compositions as described herein is administered intravenously. In some embodiments, provided compositions as described herein is administered subcutaneously. As used herein, the term "subcutaneous tissue" is defined as a layer of loose, irregular connective tissue immediately beneath the skin. For example, the subcutaneous administration may be performed by injecting a composition into areas including, but not limited to, thigh region, abdominal region, gluteal region, or scapular region. In other embodiments, provided compositions as described herein is administered by direct administration to a target tissue, such as heart or muscle (e.g., intramuscular), nervous system (e.g., direct injection into the brain; intraventricularly; intrathecally), or other target tissue such as the liver, kidney, etc. Alternatively, provided compositions as described herein can be administered via inhalation, intraperitoneally, parenterally, intradermally, transdermally, or transmucosally (e.g., orally or nasally). More than one route can be used concurrently, if desired.

In some embodiments, provided compositions, are administered in a therapeutically effective amount and/or according to a dosing regimen that is correlated with a particular desired outcome (e.g., treat dementia, improve daily function, increase in MMSE score, etc.).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of ischemic injury, etc., or combinations thereof).

In some embodiments, an appropriate dose or amount is determined in accordance with standard techniques. For example, in some embodiments, an appropriate dose or amount is a dose or amount sufficient to reduce one or more symptoms by 1, 5, 10, 15, 20, 25, 30, 35, 40, 45, 50, 55, 60, 65, 70, 75, 80, 85, 90, 95, or 100%. In some embodiments, an appropriate dose or amount is a dose or amount sufficient to maintain or prevent a decrease in scores on a test for dementia. In some embodiments, an appropriate dose or amount is a dose or amount sufficient to improve scores on a test for dementia over a baseline score taken prior to initiation of treatment. In some embodiments, an appropriate dose or amount is a dose or amount sufficient to increase MMSE score over baseline by 1, 2, 3, 4, 5, 6, 7, 9, or 10 points.

In some embodiments, an appropriate dose or amount is a dose or amount sufficient to maintain or prevent a decrease in MMSE score. In some embodiments, an appropriate dose or amount is a dose or amount sufficient to increase MMSE score over a baseline MMSE score taken prior to initiation of treatment. In some embodiments, an appropriate dose or amount is a dose or amount sufficient to result in a blood concentration of from about 1 ng/mL to about 15 ng/mL, from about 1 ng/mL to about 10 ng/mL, from about 5 ng/mL to about 15 ng/mL, or from about 5 ng/mL to about 10 ng/mL.

Alternatively or additionally, in some embodiments, an appropriate dose or amount is determined through use of one or more in vitro or in vivo assays to help identify desirable or optimal dosage ranges or amounts to be administered.

Surprisingly, as shown by the examples disclosed herein, VX-745 apparently exhibited a biphasic dose-response effect. Without wishing to be bound by any theory, it is believed that high levels of p38 MAPK activity may cause undesirably high pro-inflammatory cytokine production whereas too low p38 MAPK activity may cause an undesirable reduction of microglial activity. In various embodiments, provided compositions are administered at a therapeutically effective amount. As used herein, the term "therapeutically effective amount" or "therapeutically effective dosage amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition).

In some embodiments, a composition is provided as a pharmaceutical formulation. In some embodiments, a pharmaceutical formulation is or comprises a unit dose amount for administration in accordance with a dosing regimen correlated with achievement of disease reduction in symptoms of dementia, arrest or decrease in rate of decline of function due to dementia.

In some embodiments, a formulation comprising provided compositions as described herein is administered as a single dose. In some embodiments, a formulation comprising provided compositions as described herein is administered as two doses. In some embodiments, a formulation comprising provided compositions as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising provided compositions as described herein is administered twice weekly, thrice weekly, every other day, daily, twice daily, or every eight hours.

In some embodiments, a formulation comprising provided compositions as described herein is administered twice daily. In some embodiments, the twice daily administering occurs from about 9 to 15 hours apart. In some embodiments the twice daily administering occurs about 12 hours apart. In smile embodiments, a formulation comprising from about 40 mg to about 250 mg of VX-745 is administered twice daily. In some embodiments, the administering occurs when the patient is in a fed state. In some embodiments, the administering occurs within 30 to 60 minutes after the subject has consumed food. In some embodiments, the administering occurs when the patient is in a fasted state. The administration interval for a single individual need not be a fixed interval, but can be varied over time, depending on the needs of the individual.

In some embodiments, a formulation comprising provided compositions as described herein is administered at regular intervals. In some embodiments, a formulation comprising provided compositions as described herein is administered at regular intervals for a defined period. In some embodiments, a formulation comprising provided compositions as described herein is administered at regular intervals for 2 years, 1 year, 11 months, 10 months, 9 months, 8 months, 7 months, 6 months, 5 months, 4 months, 3 months 2 months, a month, 3 weeks, 2, weeks, a week, 6 days, 5 days, 4 days, 3 days, 2 days or a day.

Combination Therapies

In certain embodiments, the present invention provides a method of treating dementia comprising administering to a subject a dose of a p38 MAPKα inhibitor, such as VX-745, together with one or more additional therapeutic agents. In some embodiments, the present invention provides a method of treating dementia comprising administering to a subject a therapeutically effective amount of VX-745 in combination with one or more additional therapeutic agents selected from cholinesterase inhibitors, N-methyl-D-aspartate antagonists, vitamin E, antidepressants, anxiolytics, antipsychotics, mood stabilizers and sleep aids. In some embodiments, the present invention provides a method of treating dementia comprising administering to a subject a therapeutically effective amount of VX-745 in combination with one or more therapeutic agents which target amyloid and/or tau protein. In some embodiments, suitable therapeutic agents which target amyloid and/or tau protein include, but are not limited to, anti-amyloid antibodies (e.g., aducanumab), beta-secretase (BACE) inhibitors, and tau aggregation inhibitors. In some embodiments the tau aggregation inhibitor is selected from one or more of methylthioninium chloride (MTC) and LMTX®. In some embodiments, the present invention provides a method of treating dementia comprising administering to a subject a therapeutically effective amount of VX-745 in combination with a 5-$HT_6$ antagonist. In some embodiments, the present invention provides a method of treating dementia comprising administering to a subject a therapeutically of amount of VX-745 in combination with intravenous immunoglobulin (IVIg).

Representative cholinesterase inhibitors include, without limitation, donepezil (Aricept®), rivastigmine (Exelon®), galantamine (Razadyne®) and tacrine (Cognex®). Representative antidepressants include, without limitation, bupropion (Wellbutrin®), citalopram (Celexa®), fluoxetine (Prozac®), mirtazapine (Remeron®), paroxetine (Paxil®), sertraline (Zoloft®), trazodone (Desyrel®), venlafaxine (Effexor®), nortriptyline (Pamelor®) and desipramine (Norpramine®). Representative anxiolytics include, without limitation, lorazepam (Ativan®) and oxazepam (Serax®). Representative antipsychotics include, without limitation, aripiprazole (Abilify®), clozapine (Clozaril®), haloperidol (Haldol®), olanzapine (Zyprexa®), quetiapine (Seroquel®), risperidone (Risperdal®) and ziprasidone (Geodon®). Representative mood stabilizers include, without limitation, carbamazepine (Tegretol®) and divalproex (Depakota®). Representative sleep aids include, without limitation, zolpidem, zaleplon and chloral hydrate. Representative N-methyl-D-aspartate antagonists include, without limitation, memantine (Namenda®).

EXEMPLIFICATION

The following examples are provided for illustrative purposes and are not, intended to limit the scope of the invention.

Example 1

Objective

The purpose of this study was to evaluate the effects of 12-week oral twice-daily dosing on amyloid plaque load, as assessed by quantitative dynamic [$^{11}$C]PiB positive emission tomography (PET) amyloid scanning, in patients with mild cognitive impairment (MCI) due to Alzheimer's disease (AD) or with mild AD. Other objectives included development of a PK/PD model for VX-745 and amyloid plaque burden reduction, obtaining a preliminary evaluation of the safety and tolerability of VX-745 in patients with MCI due to AD or mild AD, and to evaluate the effects of VX-745 on synaptic function, as assessed by memory assessment, magnetoencephalography (MEG) and resting state fMRI. Exploratory cognitive endpoints included MMSE and Wechsler Memory Scale (WMS).

Subjects

Subjects were men and women between 60-85 years old, having a confirmed diagnosis of MCI due to AD or mild AD, a Mini-Mental State Examination (MMSE) score between 20-28 (inclusive), and demonstrated brain amyloid plaque load above a pre-determined threshold as determined by PET scan and evaluation by radiologist. FIG. 4 shows the patient demographic in this study.

Study Design

This was a Phase IIa, single-center, multiple-dose, open-label study of VX-745 (40 mg or 125 mg) administered twice daily for 12 weeks in subjects with a confirmed diagnosis of mild cognitive impairment or AD. Once eligibility was confirmed and before the first dose of VX-745, subjects were randomly assigned to one of two VX-745 dose groups and administered either 40 mg or 125 mg of VX-745 twice daily for 12 weeks. Investigators and patients were blind to the dosage strength. VX-745 capsule(s) were administered orally, twice daily with food for 12 weeks. Patients were instructed to take doses within 30 minutes following a meal or snack, with each dose taken approximately 12 hours apart at the same times each day throughout the study. Baseline MMSE score was measured in order to ensure that treatment with VX-745 did not result in detrimental effects on MMSE score, mental status, and/or mental function.

Dosing started on Day 1 following completion of all baseline procedures. During the treatment period, subjects returned to the clinic on Days 14, 28, 56, and 84. A follow-up visit was conducted 14 (±3) days following the last dose of VX-745. Dynamic PET scanning with full quantitative analysis was performed at baseline and at the end of treatment.

Target engagement was assessed through the use of an AD-related biomarker. The primary endpoint was based on assessment of amyloid plaque burden using quantitative dynamic PET amyloid scanning (Tolboom, N. et al. "Test-retest variability of quantitative [$^{11}$C]PIB studies in Alzheimer's disease." Eur. J. Nucl. Med. Mol. Imaging 36(10): 1629-1638 (2009)). The method of van Berckel et al (van Berckel B N, R. Ossenkoppele, et al. "Longitudinal amyloid imaging using $^{11}$CPiB: Methodologic considerations." J. Nucl. Med. 5=1; 1570-1576 (2013)) was followed, in which dynamic emission scanning consists of 23 frames with progressive increases in frame duration (1·15, 3·5, 3·10, 2·30, 3·60, 2·150, 2·300, and 7·600 s) for a total scan duration of 90 min; and subsequently full quantitative data analysis of the images was performed by reference parametric mapping (RPM2) using cerebellum as reference tissue. This methodology allowed for a more reliable (i.e. less variable) assessment of brain amyloid plaque load than standard amyloid PET imaging. In addition this method of measuring amyloid burden has high scan-to-scan stability (~2-3% test-test variability) within subjects. No placebo group was enrolled. Instead, reductions in brain amyloid plaque load of greater than 7%, which is definitively outside the range of test-test variability, were considered to be a drug effect in this study.

Two VX-745 doses were selected; 40 mg and 125 mg, VX-745 exposure observed in the brains of animals is approximately 1.7-fold higher than in peripheral blood.

As the primary objective of this study was to assess effects on amyloid plaque load as assessed by quantitative dynamic [$^{11}$C]PiB (carbon-11 labeled Pittsburgh Compound B) amyloid PET scanning, the major subject inclusion criteria for this study was having evidence of elevated brain amyloid plaque load by PET scanning; otherwise patients with either MCI due to AD or mild AD were included. A lower limit of MMSE score of 20 was included in order to not enroll patients with more advanced cognitive decline, in whom any potential deleterious effects of VX-745 on function would be more difficult to ascertain.

MEG and resting state fMRI are conducted to obtain initial data cm the effects of p38 MAPK inhibition by VX-745 on neuronal/synaptic function. These data can be utilized for design of additional studies that are longer in duration, larger in size, and placebo-controlled in order to further assess treatment effects of VX-745 on these measures.

Normal cognitive function in humans relies on the integration of dynamic communication between brain regions. Viewing the brain as a functional network may serve as an intermediate phenotype between pathology and clinical symptoms. Functional brain networks of healthy individuals are organized according to a highly efficient topology that optimizes local connectivity with long distance integration. In Alzheimer's Disease, among other brain diseases, changes in functional connectivity between brain regions and disruption of higher order organization of functional brain networks are seen. To measure functional connectivity and network topology, several techniques can be used, including MEG and rs-fMRI. MEG is predominantly based on the magnetic field of the summation of synaptic currents in the dendritic trees of cortical pyramidal cells, whereas fMRI measures blood oxygenation related to the levels of neural activity. Both techniques are patient friendly and have a high spatial resolution, which enables the investigation of detailed network analysis. These techniques can be used to measure VX-745 effect on the relative preservation or improvement of brain function, providing a biological indicator for study effects.

In this study, episodic memory was evaluated using the Dutch version of the WMS scale utilizing both verbal and visual information: Logical Memory (LM I & II) test, in which subject is read a story; Verbal-Paired Associates (VPA I & II), in which subject is given pairs of words and asked to remember which words go together; and Visual Reproduction (VR I & II)), in which subject is given drawings of specific shapes. Subjects were then asked to recall the information within each test both in an immediate (WMS-Immediate Recall composite) and delayed (WMS-Delayed Recall composite) basis. The total score of the WMS-Immediate Recall component could range from 0 to 136 (0-53 for LMI; 0-40 for VPA I, and 0-43 VR I) and for the WMS-Delayed Recall from 0 to 92 (0-39 for LM II; 0-10 for VPA II, and 0-43 VR II).

The 12-week treatment duration is several-fold longer than the 10-14 day treatment duration in animal studies of agents that demonstrated reduction in brain amyloid plaque load, including VX-745; 12-week treatment duration also provides a sufficient duration to assess tolerability in advance of larger and longer duration studies that would assess effects on mental status and memory function. A table summarizing the time schedule of patients assessments is provided in Table 1:

TABLE 1

Schedule of assessments Screening

| | Screening (Visit No.)[a] | | Treatment Period Visits (Study Day) Assessment Visit | | | | | Follow-Up Visit[c] |
|---|---|---|---|---|---|---|---|---|
| | 1[a] | 2[a] 3[b] | 4 | 5 | 6 | 7 | | |
| | | | Day | | | | | |
| | D −21 to D 0 | 1 | 14 | 28 | 56 | 84 | | |
| Informed Consent | X[d] | | | | | | | |
| Medical history review | X | | | | | | | |
| Prior/concomitant medication | X | X X | X | X | X | X | | X |
| Physical examination[e] | X | | | | | X | | X[f] |
| Adverse events recording[g] | X | X X | X | X | X | X | | X |
| Clinical laboratory sampling[h] | X | | X | X | X | X | X | X |
| 12-lead electrocardiogram[i] | X | | | | | | | X |
| Magnetoencephalography (MEG)[j] | | | X | | X | | X | X[f] |
| MMSE[k] | X | | X | | X | X | X | X |
| WMS (Immediate and Delayed Recall)[k] | | | X | | X | | X | X[f] |
| Dynamic ¹¹C-PiB PET scanning and resting state fMRI[l] | | X | | | | | X | X[f] |
| Dispense study drug[m] | | X | | X | X | | | |
| Pharmacokinetic sampling[n] | | | X | X | X | X | | |

TABLE 1-continued

Schedule of assessments Screening

| | Screening (Visit No.)[a] | | Treatment Period Visits (Study Day) Assessment Visit | | | | | Follow-Up Visit[c] |
|---|---|---|---|---|---|---|---|---|
| | 1[a] | 2[a] 3[b] | 4 | 5 | 6 | 7 | | |
| | | | Day | | | | | |
| | D −21 to D 0 | 1 | 14 | 28 | 56 | 84 | | |
| Plasma Tau and NFL | X | X | | | | X | | X |
| Final study drug reconciliation[m] | | | | | | X | | X[f] |

DSS: Dementia Signs and Symptoms Scale; MMSE: Mini-Mental State Examination; WMS: Wechsler Memory Scale; PET: positron emission tomography.
[a]Two screening visits are planned to allow most screening procedures to be completed and reviewed during the first visit before Dynamic Amyloid PET scan is performed. All screening assessments should be conducted within 21 days of Day 1.
[b]On Day 1, all procedures should be conducted prior to first dose of VX-745.
[c]Follow-up Visit should be conducted within 14 (±3) days of the last dose of VX-745 for subjects who complete the study or discontinue early.
[d]Informed consent procedures, including signing of informed consent, must be completed before any study-specific procedures are performed.
[e]Refer to Section 8.1.6 for details regarding physical examination
[f]These assessments will be performed at Follow-up Visit only for subjects who discontinue treatment prematurely and after day 14.
[g]Definitions and procedures for documenting and reporting adverse events and serious adverse events are provided in Sections 8.1.10 and 8.1.10.3.
[h]Details of clinical laboratory sampling for chemistry and hematology parameters are discussed in Section 8.1.8.
[i]Details of 12-lead ECG assessment are discussed in Section 8.1.7.
[j]Details of MEG are discussed in Section 8.1.2.2.
[k]Refer to the following sections for details of cognitive assessments Section 8.1.3.1 (MMSE), and Section 8.1.4.4 (WMS - Immediate and Delayed Recall).
[l]Performed concurrently on same machine; refer to Section 8.1.2.1 for details regarding 11C-PiB F18 PET scan and resting state fMRI evaluation.
[m]Study drug details including packaging, storage, accountability, and dosing are presented in Section 7.4.
[n]The time of the PK sampling and the time of the last administered dose must be recorded. Refer to Section 8.1.5 for details regarding PK sampling.

Results

Sixteen subjects completed the full 12 weeks of treatment and all were included in safety analyses. VX-745 was well tolerated. No serious adverse events were observed. FIG. 5 shows incidence of adverse events. No liver transaminase elevations were observed. In the PK analysis, due to the sparse sampling collection design, the time period from 0 to 24 hours post-dose was divided into 4 blocks in order to show the distribution of concentrations over time. In both dose groups, the time of VX-745 $C_{max}$ ($T_{max}$) was mostly observed in the 3 to 4 hours post-dose interval. Table 2 illustrates the summary statistics for VX-745 plasma concentration values. Average blood concentration of about 8 ng/mL at the 40 mg dose level was observed. This is higher than the 5 ng/mL. VX-745 $IC_{50}$ for inhibition of p38 MAPKα enzyme activity. Population pharmacokinetic analyses that combined results from this study and the study in Example 2 demonstrated a median 12-hour exposure of 78 ng*hr/mL for the 40 mg dose level and 116 ng*hr/mL for the 125 mg dose level; and a terminal half-life of approximately 16 hours.

TABLE 2

Summary Statistics of VX-745 Plasma Concentration Values Overall and for Each Dose Group by Post-dose Collection Time Interval

| | | | VX-745 Plasma Concentration (ng · hr/mL) | | | | | | |
|---|---|---|---|---|---|---|---|---|---|
| Group | Time (hours) | N | Median | Min | Max | Mean | SD | 25th | 75th |
| 40 mg | <3 | 6 | 7.66 | 5.43 | 19.10 | 9.77 | 5.09 | 6.84 | 11.07 |
| | 3 to 4 | 7 | 10.40 | 6.18 | 22.10 | 11.62 | 4.96 | 9.99 | 11.35 |

TABLE 2-continued

Summary Statistics of VX-745 Plasma Concentration Values Overall
and for Each Dose Group by Post-dose Collection Time Interval

| Group | Time (hours) | N | Median | Min | Max | Mean | SD | 25th | 75th |
|---|---|---|---|---|---|---|---|---|---|
| | >4 to <6 | 13 | 7.02 | 2.35 | 18.20 | 7.59 | 4.23 | 5.10 | 7.59 |
| | ≥6 | 9 | 4.39 | 3.01 | 8.38 | 4.95 | 1.59 | 4.15 | 4.83 |
| 125 mg | <3 | 7 | 22.10 | 9.88 | 50.10 | 24.97 | 14.47 | 14.15 | 32.20 |
| | 3 to 4 | 5 | 23.80 | 17.70 | 36.20 | 24.16 | 7.30 | 19.00 | 24.10 |
| | >4 to <6 | 13 | 14.30 | 1.84 | 35.10 | 15.37 | 8.54 | 11.40 | 17.70 |
| | ≥6 | 3 | 9.30 | 5.96 | 20.80 | 12.02 | 7.78 | 7.63 | 15.05 |
| All | <3 | 13 | 13.10 | 5.43 | 50.10 | 17.95 | 13.33 | 8.26 | 22.10 |
| | 3 to 4 | 12 | 14.95 | 6.18 | 36.20 | 16.85 | 8.63 | 10.30 | 22.53 |
| | >4 to <6 | 26 | 10.55 | 1.84 | 35.10 | 11.48 | 7.70 | 6.42 | 16.10 |
| | ≥6 | 12 | 4.80 | 3.01 | 20.80 | 6.72 | 4.80 | 4.29 | 7.01 |

FIG. 1 depicts exemplary mini MMSE parameters used in the study to assess patients to determine level of mental function.

FIG. 2 depicts an exemplary graph of absolute change in MMSE scores of four patients, treated with either 40 mg or 125 mg VX-745. As shown in FIG. 2, two of four patients in the 40 mg group surprisingly exhibited greater than a 3-point improvement in MMSE score over baseline. This finding was very surprising as no disease-modifying drug to date has shown any level of improvement in MMSE score, mental status, and/or mental function. Rather, at best all that was expected was a slowing in the rate of decline of mental function seen with dementia, particularly dementia associated with Alzheimer's disease. Without wishing to be bound by any theory, it is thought that treatment with VX-745 may enhance synaptic plasticity, stabilize and/or reverse synaptic loss, and preserve or improve neuronal function.

By observation of the descriptive MMSE data, modest changes were evident over the course of treatment. At Day 84 (Visit 7), approximately 50% of subjects in the 40 mg group and 33% of subjects in the 125 mg group had an increase from screening of at least 1 in MMSE score.

Figure 6:
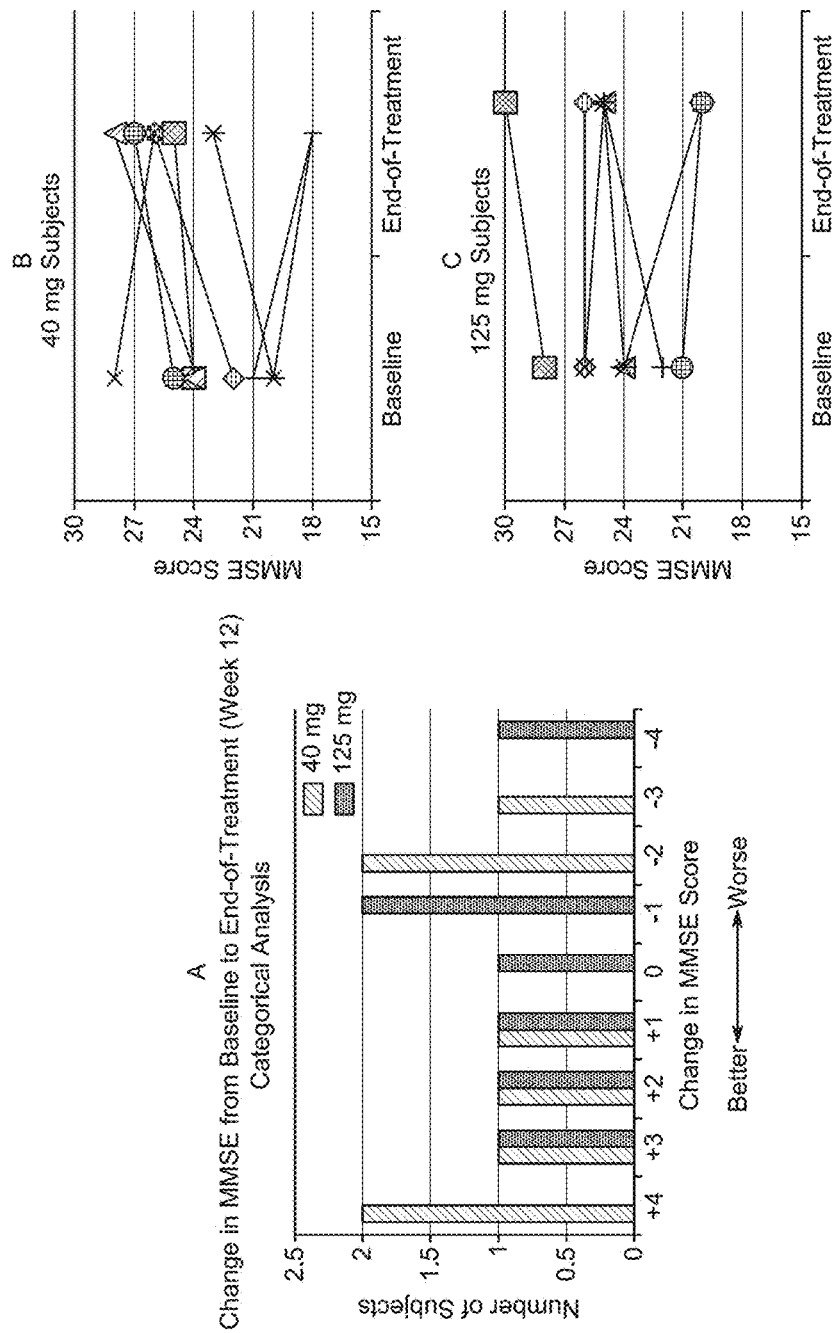
FIG. 6 panels A-C depict changes in MMSE scores for eight patients treated with 40 mg and seven patients treated with 125 mg VX-745.

FIG. 6 panels A-C depict changes in MMSE scores for eight patients treated with 40 mg and seven patients treated with 125 mg VX-745.

Further analysis included Wechsler Memory Scale (WMS) Analyses. The WMS includes three subcategories: immediate recall, delayed recall, and symbol span, each with distinct assessments. Results can be analyzed as two distinct composites scores or as an overall composite score. This evaluation included the overall (score range: 0 to 401), immediate recall (score range: 0 to 136), and delayed recall (score range: 0 to 92) composite scores; the latter two are considered measures of episodic memory. In addition, the Symbol Span sub-component of WMS was analyzed separately (score range: 0 to 50). In all cases, higher scores reflect better cognitive performance.

Mean Wechsler Memory Scale (WMS) immediate recall composite scores increased from 48.4 (±3.8) at baseline to 58.4 (±4.3) at Day 84 (n=15; p=0.005 by Wilcoxon sign rank test for improvement). Mean WMS delayed recall composite scores increased from 13.2 (±2.3) at baseline to 22.1 (±4.1) at Day 84 (p<0.001.). For immediate recall composite score, 7 of 8 patients in the 40 mg group and 6 of 7 in the 125 mg group showed improvement from baseline and, for delayed recall composite score, 8 of 8 patients in the 40 mg group and 6 of 7 in 125 mg group showed improvement from baseline.

P-values based on Wilcoxon-signed rank one-sided test for median change from baseline are presented in Table 3. Statistically significant improvement (P value≤α at 0.05 level) was observed for combined dose groups (N=15) for all composite scores on Day 84. The increase from baseline to Day 84 in overall composite score was statistically significant individually for the 40 mg (P=0.021) and 125 mg (P=0.017) groups, and for immediate-recall composite within 125 mg group (P=0.026), and for delayed-recall composite within 40 mg (P=0.007) and 125 mg groups (P=0.013); a trend (P=0.054) was seen for 40 mg dose for immediate-recall composite change from baseline to Day 84. Episodic memory within the WMS showed improvement. All subcomponents of WMS episodic memory composites showed statistically significant (P<0.05) increases at Day 84.

TABLE 3

P-Value for Testing Wechsler Memory Scale Median Increase from
Baseline in Composite Scores (Immediate Recall, Delayed Recall,
and Overall) and Symbol Span by Visit and Treatment

| | | P-value | | |
|---|---|---|---|---|
| Score | Visit | 40 mg | 125 mg | All |
| Immediate Recall Composite | 5 (Day 28) | 0.200 | 0.037 | 0.028 |
| | 7 (Day 84) | 0.054 | 0.026 | 0.005 |
| Delayed Recall Composite | 5 (Day 28) | 0.007 | 0.071 | 0.001 |
| | 7 (Day 84) | 0.007 | 0.013 | 0.000 |
| Symbol Span | 5 (Day 28) | 0.612 | 0.011 | 0.116 |
| | 7 (Day 84) | 0.879 | 0.304 | 0.546 |
| Overall Composite | 5 (Day 28) | 0.080 | 0.011 | 0.003 |
| | 7 (Day 84) | 0.021 | 0.017 | 0.002 |

Note:
P-value is based on Wilcoxon signed rank test that tested for improvement (1-sided)

Figure 7:
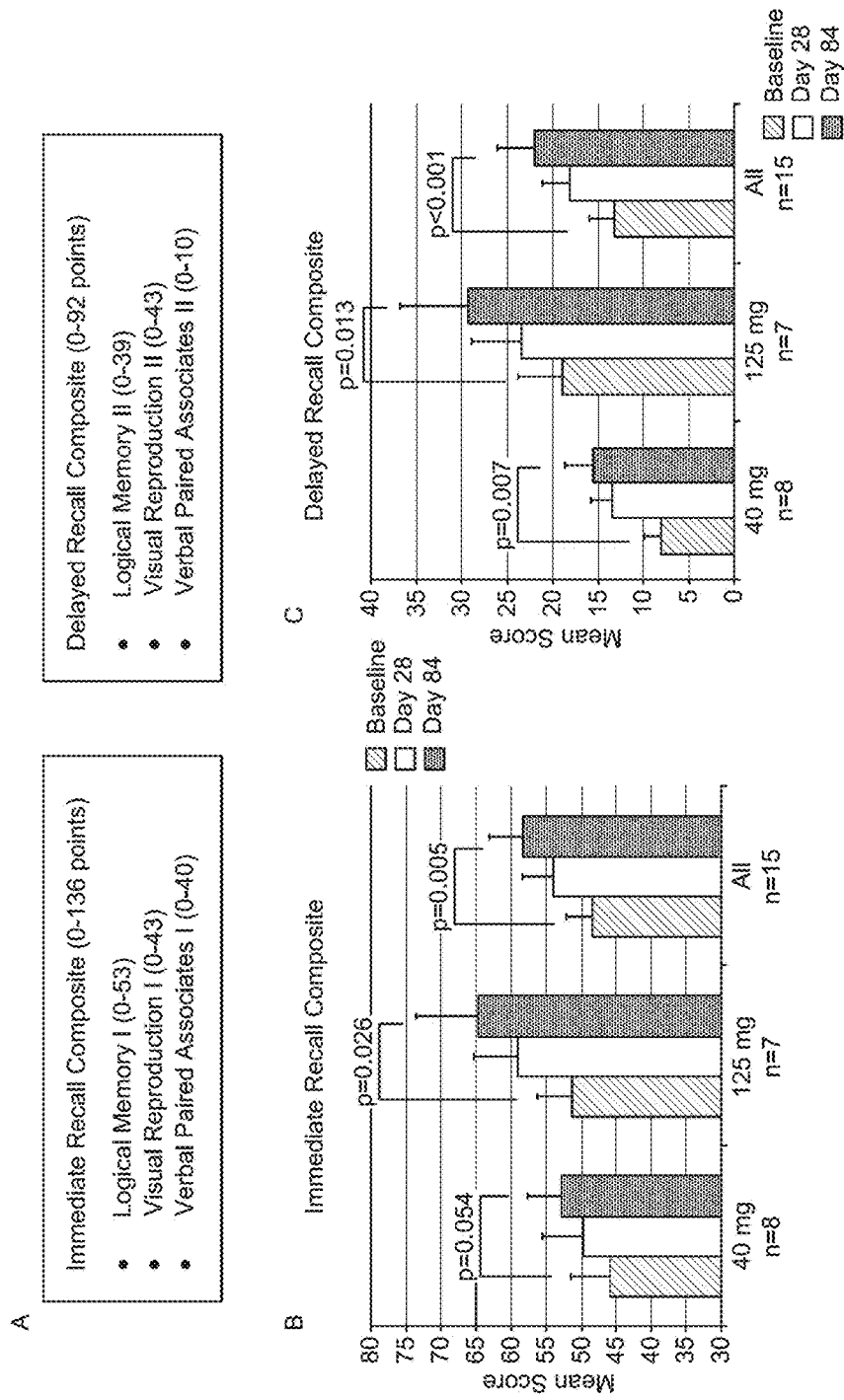
FIG. 7 shows Wechsler Memory Scale (WMS) Analyses. (A) shows three subsets of the WMS test (Logical Memory, Visual Reproduction, and Verbal Paired Associates) and associated point-based performance scores for immediate recall and delayed recall indices. (B) depicts the Immediate Recall mean scores for subjects administered 40 mg or 125 mg VX-745. (C) depicts the Delayed Recall mean scores. Analyses were done by Wilcoxon sign rank test for improvement.

FIG. 7 shows Memory Scale (WMS) Analyses. Cognitive, analysis showed dose dependent improvement on immediate and delayed recall in nearly all patients, regardless of effect on amyloid plaque. (A) shows three subsets of the WMS test (Logical Memory, Visual Reproduction, and Verbal Paired Associates) and associated point-based performance scores for immediate recall and delayed recall indices. (B) depicts the Immediate Recall mean scores for subjects administered 40 mg or 125 mg VX-745. Improvement from baseline at day 84 was observed in 7 of 8 patients in the 40 mg group and 6 of 7 in the 125 mg group. (C) depicts the Delayed Recall mean scores. Improvement from baseline at day 84 was observed in 8 of 8 patients in the 40 mg group and 6 of 7 in the 125 mg group. Analyses were done by Wilcoxon sign rank test for improvement.

PK-PD modeling demonstrated that exposure (AUC) of VX-745 was a statistically significant variable for predicting the change from baseline to Day 84 in combined WMS immediate and delayed recall score. Plasma drug levels explained 70% (i.e., $r^2$=0.70; P=0.0001) of the variance in change (improvement) from baseline to end-of-treatment. Therefore, PK-PD correlation (linear-regression model) indicated individual subject plasma drug concentration profiles were significantly correlated to change in combined WMS immediate-and delayed-recall. These data strongly argue that the improvement seen in episodic memory in this study was primarily due to VX-745 treatment, and not due to chance or practice effects.

Figure 8:
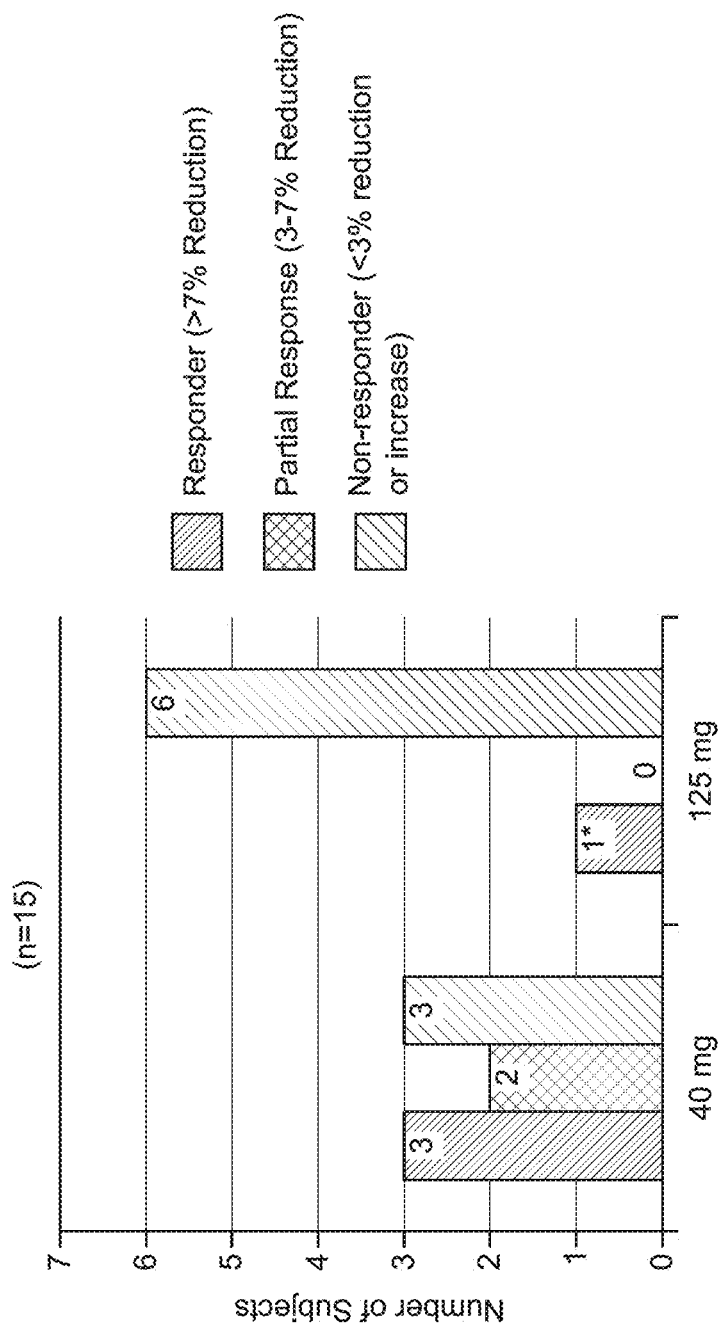
FIG. 8 depicts responder analysis of dynamic [$^{11}$C]PiB PET.

FIG. 8 depicts responder analysis of dynamic [$^{11}$C]PiB PET. Response is defined by % Change RPM2_BPND parameter from quantitative analysis of dynamic PET Scan. On 40 mg, 3 subjects reached the 7% responder criterion and 2 subjects were between 3 and 7%. Subject with response on 125 mg had the lowest plasma drug exposure in that group; drug exposure in this subject approximated that in 40 mg dose group.

The heterogeneous response is consistent with the model in which the primary relevant pharmacological effect is a decrease in amyloid plaque production, which in the context of efficient endogenous clearance would lead to reduced brain amyloid plaque load. However, the level of endogenous clearance will vary for patient to patient. Consistent with this hypothesis the responders were all patients with lower levels of baseline brain amyloid plaque load less than the median for the study, as these would be the patients that would be expected to have higher endogenous amyloid plaque clearance levels at study entry.

Percentage reduction in global cortical RPM2-BPND in the 3 responders in the 40 mg dose group was −11.6%, −11.9%, and −40.5%, respectively, and in the one responder in the 125 mg dose group was −7.7%. Results were similar for response rate for all regional measurements of PET metrics. Table 4 summarizes responders.

TABLE 4

Number of Responders by PET Metric and Dose Group and Overall

| PET Metrics | Number of Responders$^a$/Total Number in Population | | |
|---|---|---|---|
| | 40 mg | 125 mg | All |
| Global | 3/8 | 1/7 | 4/15 |
| Frontal | 3/8 | 1/7 | 4/15 |
| Med Temp Lobe | 4/8 | 2/7 | 6/15 |
| Temporal | 2/8 | 1/7 | 3/15 |
| Cingulate Posterior | 2/8 | 0/7 | 2/15 |
| Parietal | 3/8 | 0/7 | 3/15 |

Source: Listing 16.2.6.1
$^a$Responder was defined as reduction of ≥7% in PET metrics (RPM2-BPND).

Figure 9:
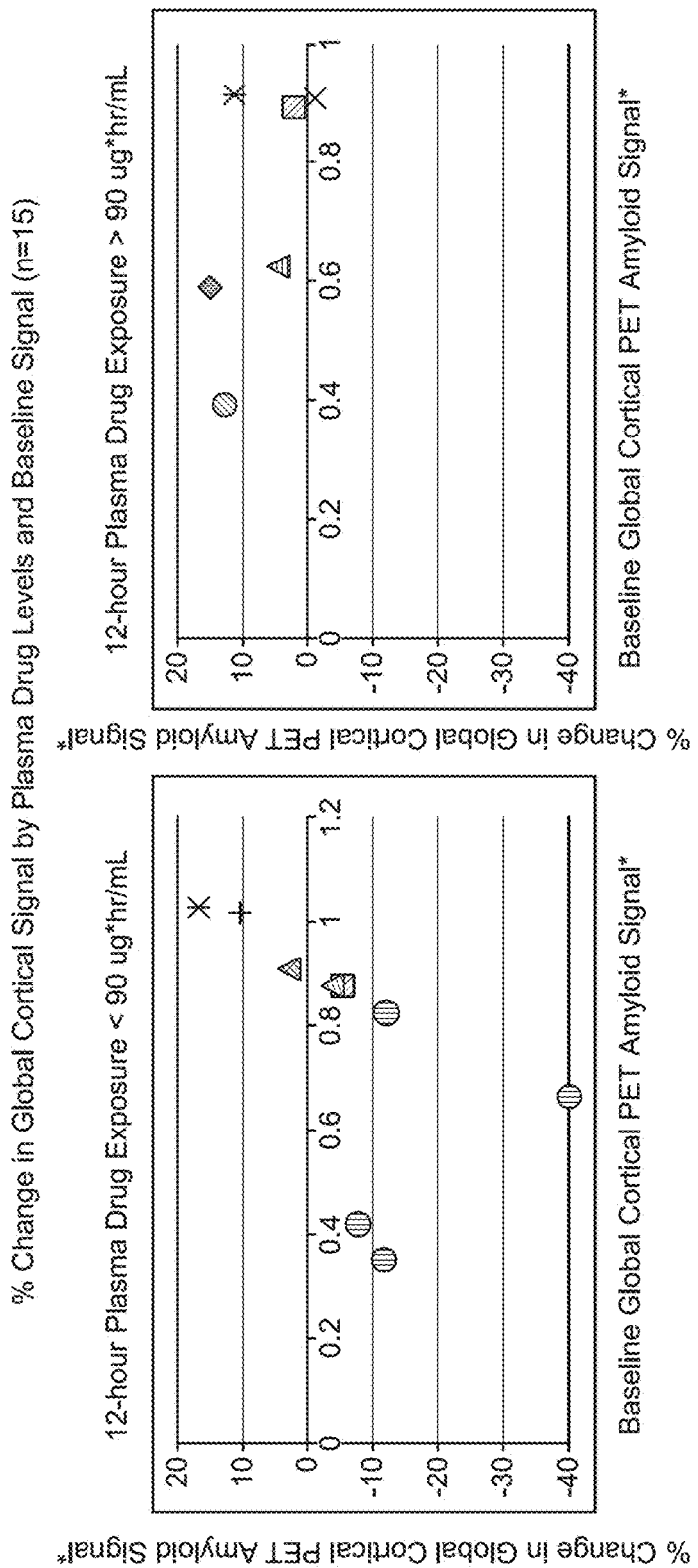
FIG. 9 depicts analysis of quantitative dynamic [$^{11}$C]PiB PET. Shown are receptor parametric mapping (RPM2)_BPND parameters from quantitative analysis of dynamic PET Scan. Percent change in global cortical PET amyloid signal versus baseline signal is depicted for <90 μg*hr/mL and >90 μg*hr/mL in a 12-hour plasma exposure to VX-754. Responders are shown as circles with vertical lines.

FIG. 9 depicts analysis of quantitative dynamic [$^{11}$C]PiB PET. Shown are RPM2_BPND parameters from quantitative analysis of dynamic PET Scan. Percent change in global cortical PET amyloid signal versus baseline signal is depicted for <90 µg*hr/mL and >90 µg*hr/mL in a 12-hour plasma exposure to VX-754. Responders are shown as circles with vertical lines. Potential explanations for lack of effect at <90 µg*hr/mL at high baseline cortical PET signal may indicate high plaque loads outside the dynamic range of the test and/or 3-month treatment duration that is not sufficient for effect on higher plaque loads.

Figure 15:
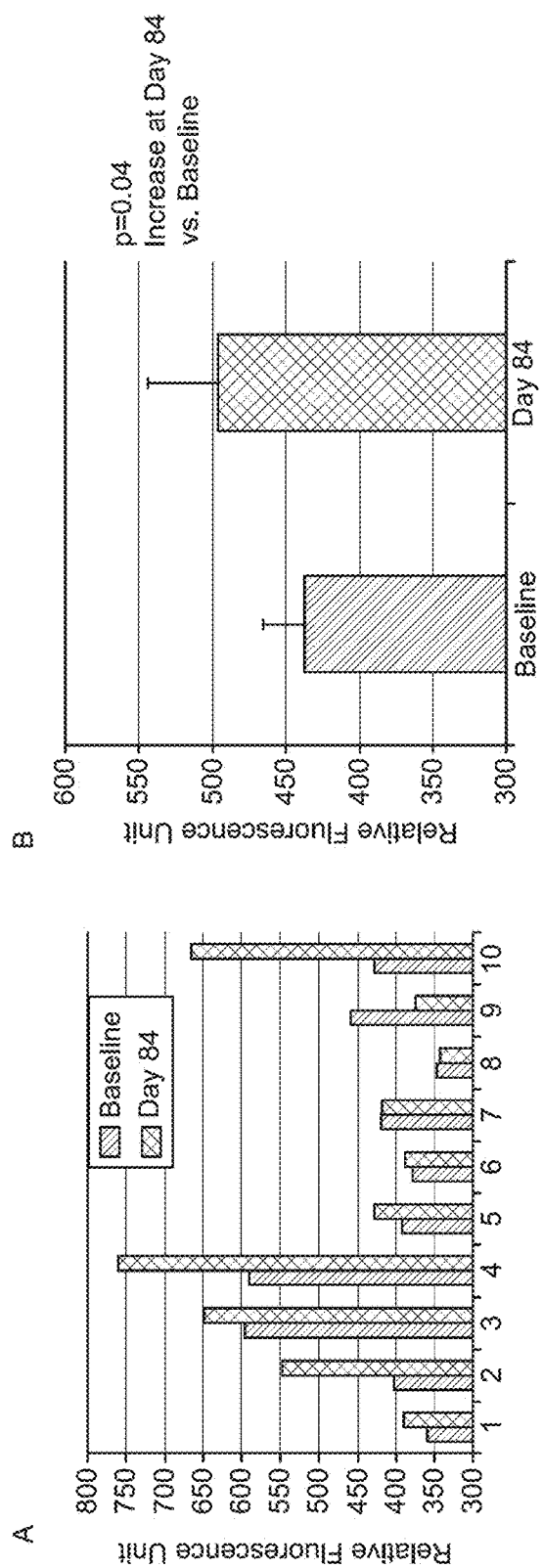
FIG. 15 depicts plasma brain-derived neurotrophic factor (BDNF) levels at baseline and after 84 days (n=10 subjects). (A) shows individual subject BDNF levels. (B) shows mean BDNF levels.

FIG. 15 depicts plasma brain-derived neurotrophic, factor (BDNF) levels at baseline and after 84 days (n=10 subjects). BDNF levels were measured by Somascan®. (A) shows individual subject BDNF levels. (B) shows mean BDNF levels. These results indicate that VX-745 at this dose increases plasma BDNF levels in humans.

Example 2

Objective

The purpose of this study was to assess the pharmacodynamic (PD) activity of VX-745 in the central nervous system of patients with mild cognitive impairment (MCI) due to Alzheimer's disease (AD) or with mild AD. Other objectives included evaluating the safety and tolerability of VX-745 at doses of 40 and 125 mg twice daily for 6 weeks (42 days) in patients with a confirmed diagnosis of mild cognitive impairment due to AD or with mild AD and evaluating the plasma and cerebrospinal fluid (CSF) pharmacokinetic profile of VX-745 at doses of 40 and 125 mg administered twice daily for 6 weeks (42 days) in patients with a confirmed diagnosis of MCI due to MD or with mild AD. Exploratory cognitive endpoints included Hopkins Verbal Learning Test-Revised (HVLT-R) and MMSE.

Subjects

Subjects were men and women between 60-85 years old, having a confirmed diagnosis of MCI due to AD or mild AD (consistent with National Institute of Aging and Alzheimer's Association research diagnostic guidelines) and a Mini-Mental State Examination (MMSE) score greater than 20. Inclusion criteria included gradual and progressive decline in memory function reported by patients or informants over more than 6 months; an amnestic presentation on formal neuropsychological testing that was characterized by a pattern of rapid forgetting, as determined by the PI/subinvestigator; evidence of functional decline as evidenced by a CDR sum of box score of ≥0.5; and MMSE score of 17 to 30, inclusive. FIG. 10 shows the patient demographic in this study. A total of 9 subjects were enrolled and all were included in safety analysis; 8 subjects completed 6 weeks treatment and were included in pharmacodynamics analysis. As plasma drug concentration in the one subject who received 125 mg was similar to the remaining study subjects, this subject's data were pooled with the remaining subjects in all analyses.

Study Design

This is a phase IIa, single center, multiple-dose, open-label study of VX-745 (40 mg or 125 mg) administered twice daily with meals for 6 weeks (42 days) in subjects with a confirmed diagnosis of mild cognitive impairment due to AD or mild AD. Once eligibility was confirmed and before baseline CSF sampling, subjects were randomly assigned to one of two NIX-745 dose groups and administered either 40 mg or 125 mg of VX-745, twice daily for 12 weeks. Investigators and patients were blinded to the dosage strength. The first 3 patients were randomly assigned to receive either 40 or 125 mg twice daily, with dosing level blinded. The remaining patients (up to 7 patients) received 40 mg twice daily on an open-label basis. After the baseline CSF sampling, VX-745 capsule(s) were administered orally, twice daily with food for 6 weeks. Patients were instructed to eat a meal approximately 30 minutes before dosing with VX 745 with each dose taken approximately 12 hours (+/−3 hours) apart at the same times each day throughout the study.

Cytokine measurements of CSF samples were done to assess the balance of pro-inflammatory versus anti-inflammatory cytokines. The t-helper type 1/t-helper type 2 (TH1/TH2) multiplex cytokine (IFN-γ, IL-1β, IL-2, IL-4, IL-5, IL-8, IL-10, IL-12p70, IL-13, TNFα) panel by Mescoscale Discovery were utilized to inform on effects on the relative balance of pro-inflammatory cytokines (e.g. IL-1β, TNFα) versus anti-inflammatory cytokines (e.g., IL-10).

Effects on CSF levels of Aβ peptides were evaluated as measures of the amyloidenic process, which is activated with aging and more so in patients with Alzheimer's disease.

Phospho-tau and NFL proteins from CSF sampling were evaluated as markers of the effects of inflammation on neurodegeneration and axonopathy, respectively. The CSF-NFL marker has been demonstrated in other neuro-inflammatory disease contexts to be a sensitive and specific marker of inflammation-induced axonal damage.

Butylcholinesterase expression on microglia has been demonstrated in animal studies and in human brain to be associated with pro-inflammatory microglial activation, and CSF measurements of butylcholinesterase were available as indirect measures of activation in the brain. Quantitative EEG was conducted as a measure of the effects of inflammatory cytokines on synaptic function and the effects of modulation of p38 MAPK on synaptic plasticity. Brain fluorodeoxyglucose (FDG) PET scan was conducted at the Screening Visit and Day 40 to measure brain metabolism. In addition, CSF drug levels of VX-745 were obtained to confirm delivery of drug to the brain.

Results

VX-745 was well-tolerated. No safety concerns were identified. One subject discontinued within the first week because of headache and vomiting, attributed to persistent CSF leak after baseline CSF collection. Most common adverse events included mild dizziness, headache, and somnolence reported in 2 subjects each. There were no treatment-related or clinically relevant trends for any of the safety laboratory or 12-lead ECG parameters.

Plasma pharmacokinetics indicated that average blood drug concentration ($C_{AVG}$) at 40 mg was 8 ng/mL and Cmax was 23 ng/mL. A weight of <57 kg was associated with higher plasma drug concentrations. The terminal half-life was 10 hours. CSF drug levels were 6% of plasma drug levels at the same time point. This was consistent with preclinical CSF PK data, which were associated with brain concentrations two-fold higher than that in blood. Thus, VX-745 concentrations in the brain are expected to be at ~14 ng/mL (~30 nM), which is the concentration that cart inhibit IL-1β signaling.

Target engagement was assessed through the evaluation of the effect of drug treatment on CSF biomarkers. CSF was collected at 6 time-points over 24 hours at baseline (the 24 hours prior to first dose) and again at 6 time-points over 24 hours near the end of treatment on Day 40. The samples were evaluated by the Mesoscale Discovery ELISA platform for multiple cytokines ((IFN-γ, IL-1β, IL-2, IL-4, IL-5, IL-8, IL-12 protein 70, IL-13, TNFα, and CSF) and for amyloid-beta peptides (Aβ 38/40/42).

Figure 11:
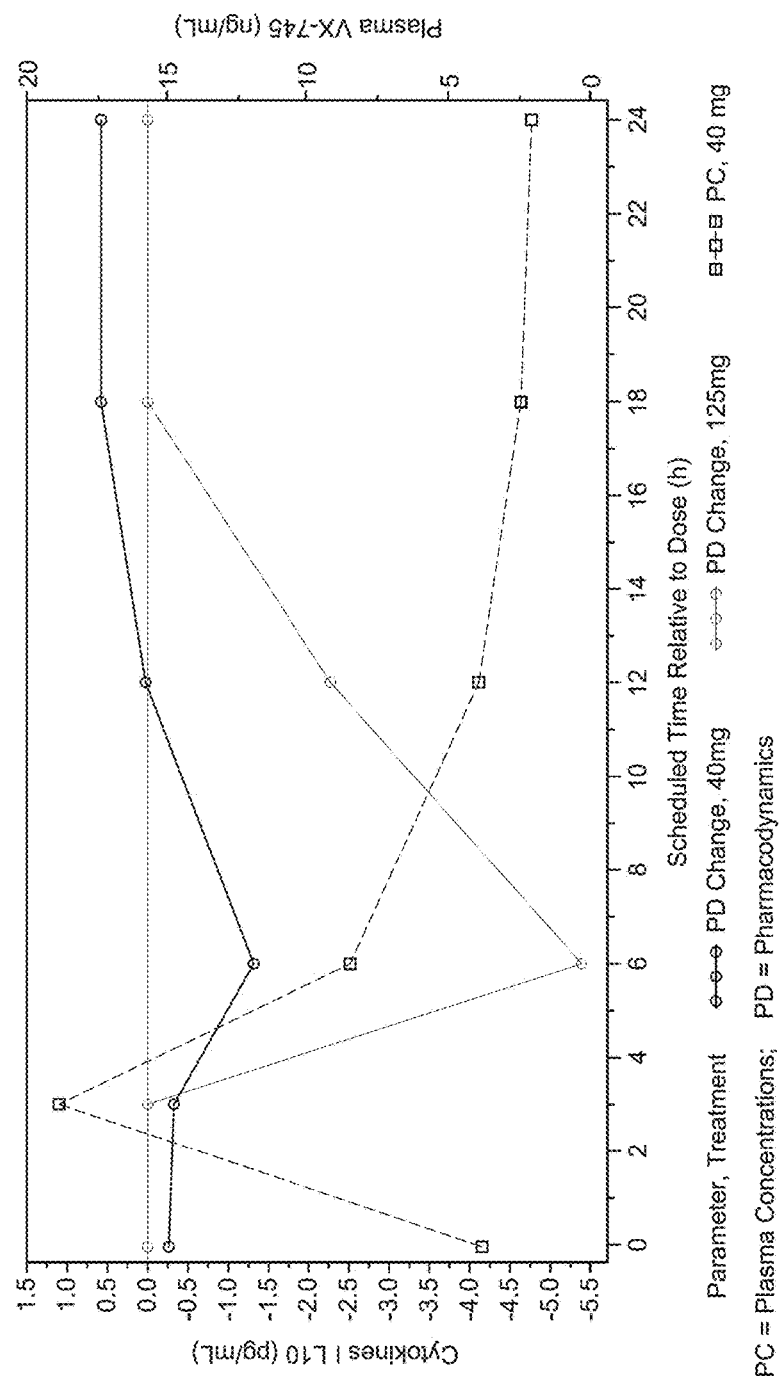
FIG. 11 depicts CSF interleukin-10 (IL-10) mean change from baseline on day 41 with time-matched day 42 plasma concentration.

FIG. 11 depicts CSF interleukin-10 (IL-10) mean change from baseline on day 41 with time-matched day 42 plasma concentration. CSF IL-10 decreased rapidly after VX-745 reached Cmax in the plasma. The decrease appears to increase with dose; however, there is only 1 patient at 125 mg.

Of the cytokines evaluated, only IL-8 and TNFα were consistently detectable in all subjects. For each there was a statistically significant correlation ($p=0.004$ and $p=0.04$, respectively) between plasma drug concentration and suppression of peak levels at the Day 40.

Figure 12:
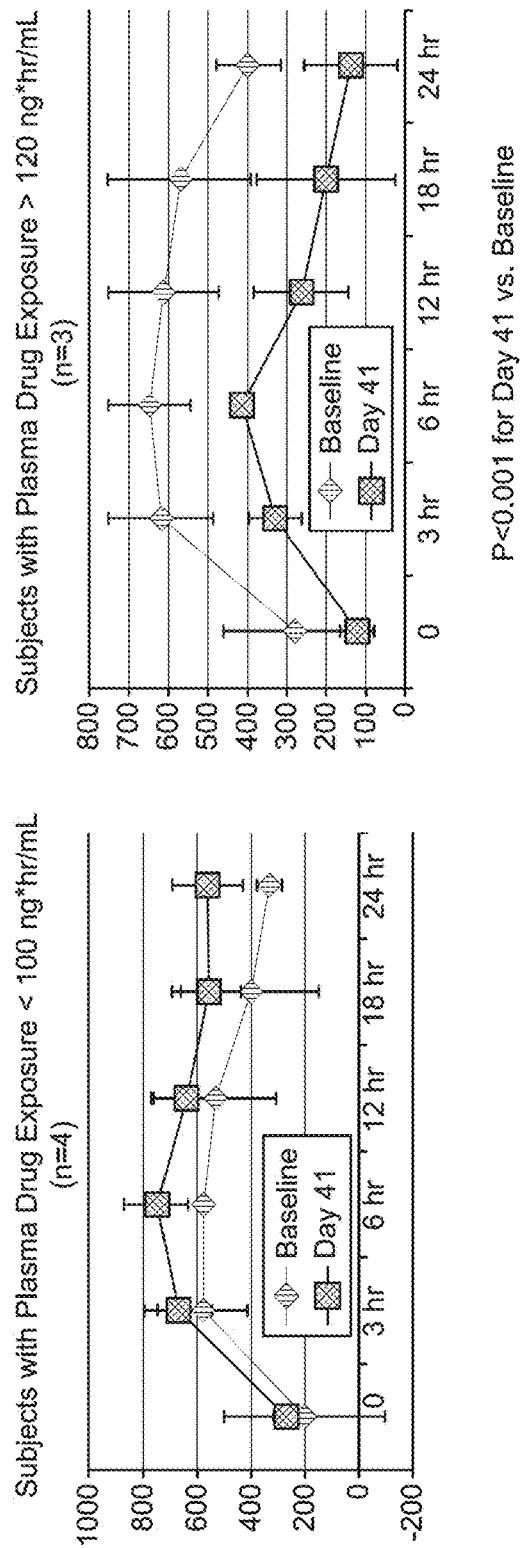
FIG. 12 depicts interleukin-8 (IL-8) levels (pg/mL) CSF over 24 hours at baseline and at day 41.

Separating patients into high and low exposure groups based on plasma $AUC_{(0-8)}$ on Day 1, comparison concentrations at matched time points at Day 41 to baseline lead to a trend towards lower CSF IL-8 in the high exposure group. FIG. 12 depicts interleukin-8 (IL-8) levels (pg/mL) CSF over 24 hours at baseline and at day 41.

For Aβ 38/40/42, there was a statistically significant correlation ($p=0.01$ to $p=0.047$) between plasma drug concentration and increases from baseline to Day 41 in levels of each Aβ peptides.

The combined effect of a reduction of CSF inflammatory markers and an increase in CSF Aβ peptides suggests that higher plasma drug concentrations ($AUC_{0-12}$>120 ng*hr/mL) leads to inhibition of microglial activation. Inhibition of microglia activation may explain why the 125 mg dose level appeared to not be effective in reducing brain amyloid plaque load in Example 1.

The Hopkins Verbal Learning Test-Revised (HVLT-R) was utilized to assess episodic memory. In this test, 12 specific words from a list were provided verbally, and the subject was asked to recall as many words as possible. Two scores are calculated: (i) Total (Immediate) Recall Score (range: 0-36): combined score of three consecutive trials immediately following provision of words and (ii) Delayed Recall Score (range: 0-12): Number of words recalled when subject was asked 20 to 25 minutes after initial trials to recall as many of the words originally provided. A strength of the HVLT-R is that six different validated version exist that each incorporate a different set of words. Due to the use of these different versions during the course of a clinical study, there is essentially no practice effect with repeated administration (Benedict, R. H. B. et al, "Hopkins Verbal Learning Test-Revised: Normative Data and Analysis of Inter-Form and Test-Retest Reliability" The Clinical Neuropsychologist, 12(1): 43-55 (1998)).

Mean Total Recall improved from 19.1 (±1.5) at Baseline to 22.6 (±2.1) at week 6 ($p=0.015$ for improvement from baseline); Delayed Recall increased from 5.4 (±0.6) to 7.5 (±1.1) ($P=0.028$ for improvement from baseline). Median increase in Total Recall score was 4.5 (range: −2.5 to +9.5), with only one subject with a decrease during treatment. Particularly with the use of alternate versions that should minimize "placebo effects", the consistency of improvement and statistics indicates that the improvements in episodic memory seen in this study are due to VX-745 treatment (Table 5).

TABLE 5

Hopkins Verbal Learning Total Recall, Delayed Recall, Retention and Recognition Scores Change from Averaged Baseline - Overall (Pharmacodynamic Population)

| HVLT-R Score Visit | n | Arithmetic Mean | SD | 90% CI Lower Bound | 90% CI Upper Bound | P Value | Minimum | Median | Maximum |
|---|---|---|---|---|---|---|---|---|---|
| Total Recall | | | | | | | | | |
| Day 14 | 8 | 0.6 | 2.62 | −1.13 | 2.38 | 0.2604 | −2 | 0.0 | 6 |
| Day 40 | 8 | 3.5 | 3.61 | 1.08 | 5.92 | 0.0143 | −3 | 4.5 | 10 |
| Delayed Recall | | | | | | | | | |
| Day 14 | 8 | 0.8 | 1.83 | −0.48 | 1.98 | 0.1425 | −3 | 1.0 | 4 |
| Day 40 | 8 | 2.1 | 2.62 | 0.37 | 3.88 | 0.0276 | 0 | 1.0 | 7 |

TABLE 5-continued

Hopkins Verbal Learning Total Recall, Delayed Recall, Retention and Recognition
Scores Change from Averaged Baseline - Overall (Pharmacodynamic Population)

| HVLT-R Score Visit | n | Arithmetic Mean | SD | 90% CI Lower Bound | 90% CI Upper Bound | P Value | Minimum | Median | Maximum |
|---|---|---|---|---|---|---|---|---|---|
| Retention (%) | | | | | | | | | |
| Day 14 | 8 | 3.8 | 24.50 | −12.66 | 20.16 | 0.3390 | −37 | 6.3 | 35 |
| Day 40 | 8 | 15.3 | 26.61 | −2.58 | 33.08 | 0.0746 | −14 | 6.5 | 71 |
| RDI | | | | | | | | | |
| Day 14 | 8 | −0.1 | 2.28 | −1.65 | 1.40 | >0.5 | −3 | −0.3 | 5 |
| Day 40 | 8 | −1.3 | 5.82 | −5.15 | 2.65 | >0.5 | −11 | 1.3 | 6 |

CI = confidence interval for the mean:
P value: statistical significance (1-sided) for test that paired mean difference is improved (increased) versus a null hypothesis of no improvement:
RDI = Recognition Discrimination Index:
SD = standard deviation:
n = number of patients in the specific population
Baseline is the average of Screening and Day −2.

Figure 13:
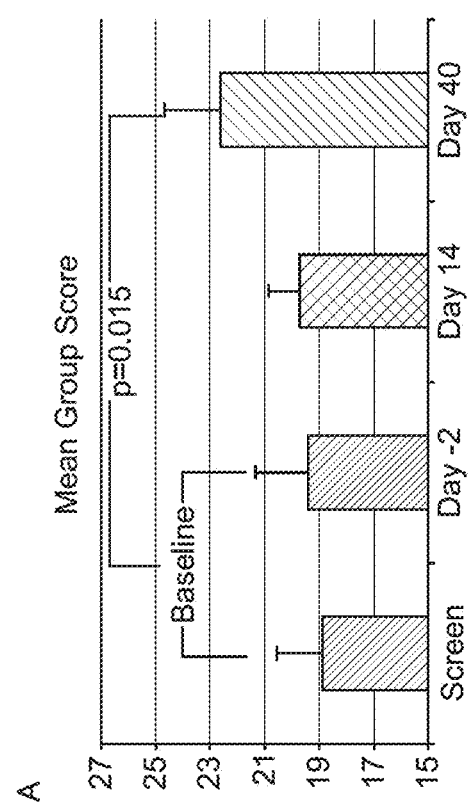
FIG. 13 comprising panels A-D, depicts Hopkins Verbal Learning Test-Revised (HVLT-R) analyses. (A) shows mean group scores for HVLT-R total recall. For each subject, baseline is calculated as an average of the screening and day −2 value (n=8). (B) shows individual subject scores for HVLT-R total recall. (C) shows mean scores for HVLT-R total recall. (D) shows mean group scores for HVLT-R delayed recall. For each subject, baseline is calculated as an average of the screening and day −2. value (n=8). (E) shows individual subject scores for HVLT-R delayed recall. (F) shows mean scores for HVLT-R delayed recall.
Figure 13:
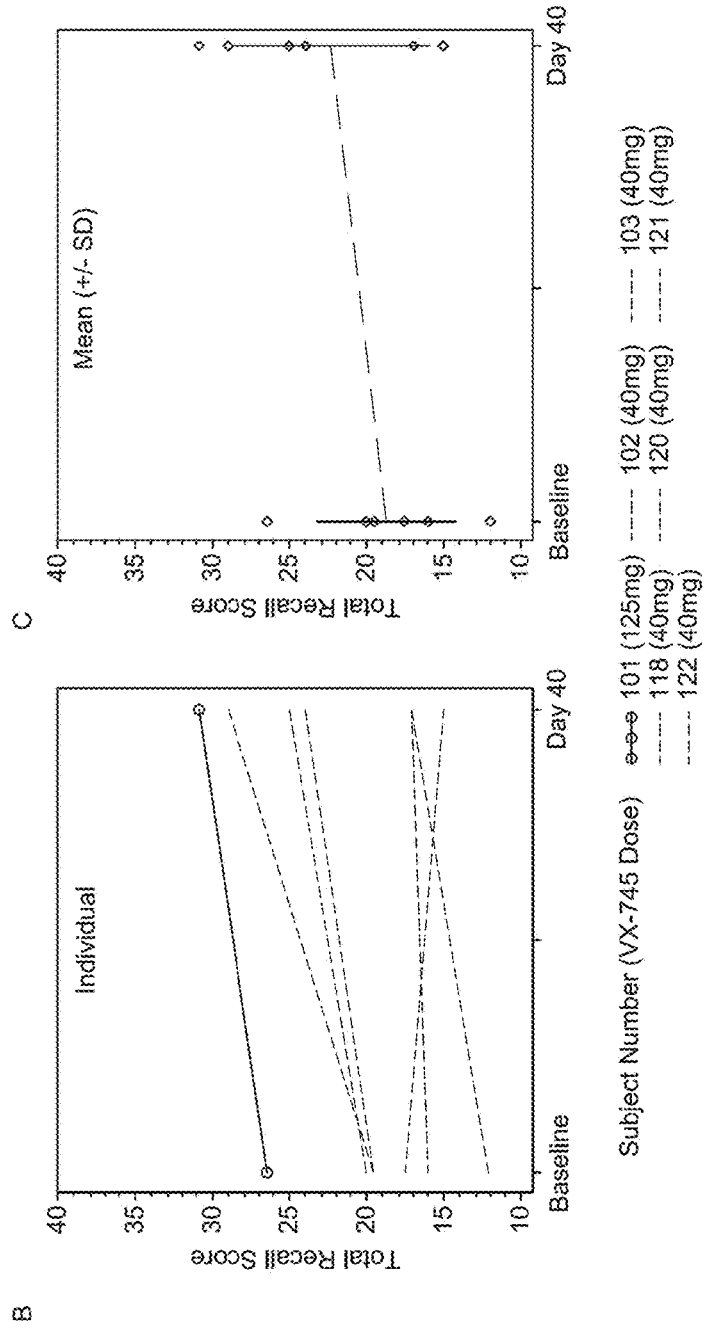
Figure 13:
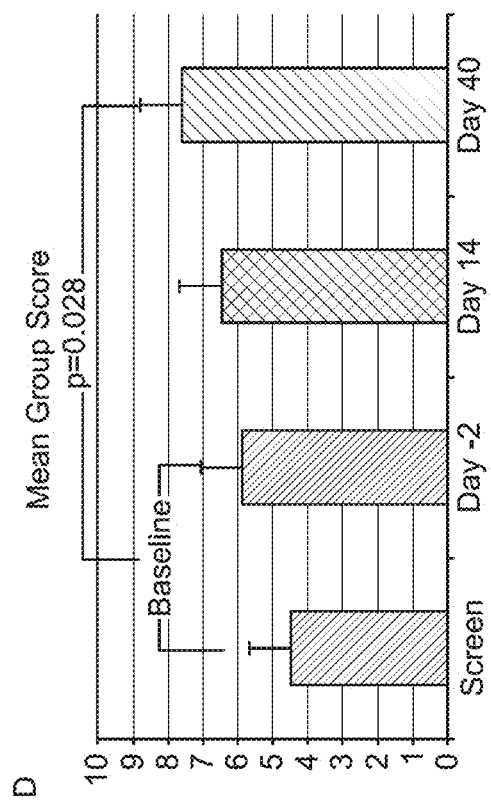
Figure 13:
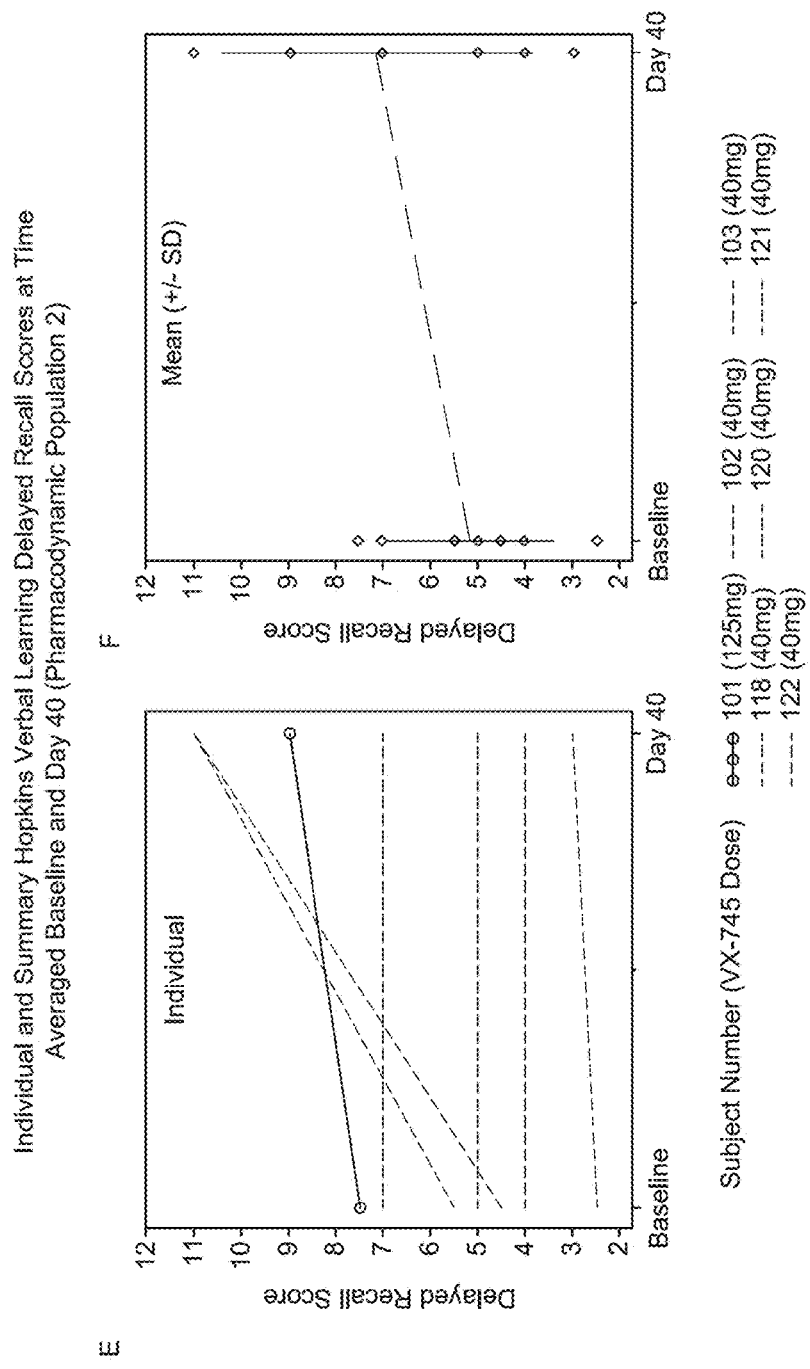

FIG. 13 depicts Hopkins Verbal Learning Test-Revised (HVLT-R) analyses. (A) shows mean group scores for HVLT-R total recall. For each subject, baseline is calculated as an average of the screening and day −2 value (n=8). During screening (dates −28 to −3), patients underwent eligibility procedures, including screening for concomitant medications and medical assessments including vital signs, 12-lead electrocardiogram, physical exam, clinical laboratory testing, and FDG PET scan. On day −2. in screening procedures were repeated, but instead of FDG PET scan, patients were given quantitative electroencephalogram (qEEG), Hopkins Verbal Learning Test-Revised (HVLT-R) and Columbia-Suicide Severity Rating Scale (C-SSRS). (B) shows individual subject scores for HVLT-R total recall. (C) shows mean scores for HVLT-R total recall. (D) shows mean, group scores for HVLT-R delayed recall. For each subject, baseline is calculated as an average of the screening (days −28 to −3) and day −2 value (n=8). (E) shows individual subject scores for HVLT-R delayed recall. (F) shows mean scores for HVLT-R delayed recall.

To further evaluate and compare the episodic memory results, within-subject treatment effect sizes (ES; called Cohen's d in statistics) were calculated for each study (Example 1 and Example 2)/measure. The results are shown in Table 6.

TABLE 6

Calculated Treatment Effect Sizes.

| | Example 1 study (N = 15) (Wechsler Memory Scale) | Example 2 study (N = 8) (HLVT-R) |
|---|---|---|
| Immediate Recall | .59 | .69 |
| Delayed Recall | .69 | .86 |

The within-subject effect size (ES) calculations show first that the results are very similar between the two studies, i.e. there is a high degree of consistency between the studies despite the use of different measures and tests being applied in different languages/cultures. The magnitude of the ES ranging between 0.59 and 0.86 also argues for a true drug effect as in MCI and AD patient population ES for improvement in placebo groups when they are seen are less than 0.3 (Goldberg et al, 2015), and often show either no change or worsening (Scheltens et al, 2011; Hassenstab et al, 2015).

In addition, as ES>0.5 is generally taken as being clinically meaningful, ES calculations allows an assessment of whether the magnitude of treatment effect is clinically relevant; which in the current clinical studies with VX-745 appears to be so. An ES relative to placebo-treatment may be determined with a randomized-double-blind placebo-controlled study.

Figure 14:
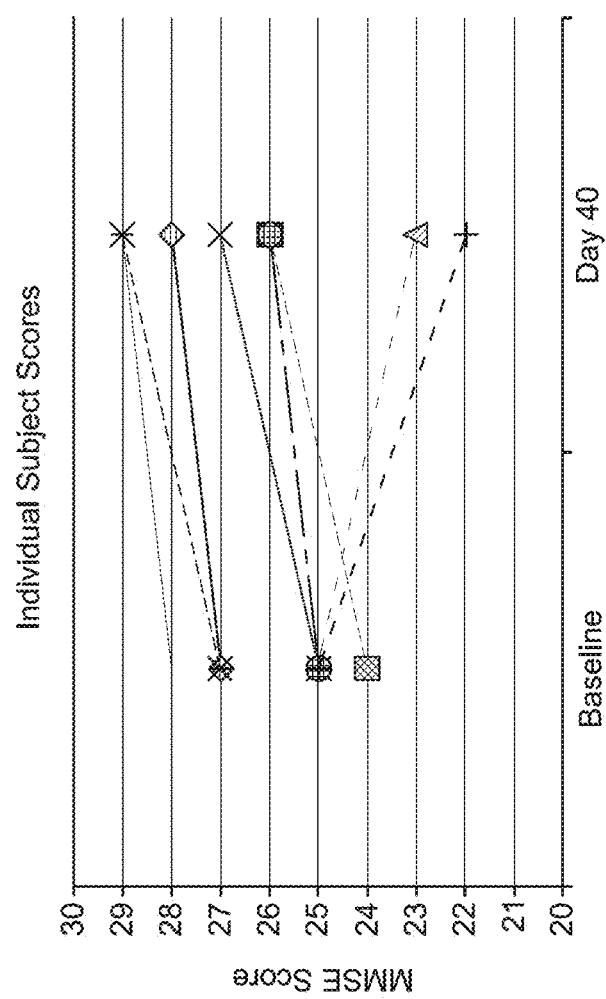
FIG. 14 depicts MMSE individual subject scores at baseline and day 40.

FIG. 14 depicts MMSE individual subject scores at baseline and day 40. Although the variability in MMSE results and the sample sizes tdo not allow statistical analyses, the overall trends are encouraging. CSF levels of neurofilament light chain (NFL) and butylcholinesterase showed no change from baseline to day 40FDG-PET showed no change from baseline to day 40. EEG showed potential positive pharmacodynamics effect.

Example 3

Objective

A six-month study is performed to establish that VX-745 can improve mental functions impaired by dementia. Fifty (50) to 100 patients diagnosed with MCI or dementia associated with Alzheimer's disease are assigned to each treatment arm: placebo vs. 40 mg of VX-745.

Subjects

Subjects are men and women with clinically diagnosed late MCI or mild Alzheimer's disease, having MMSE score above 20, FSCRT free recall below 20, total recall below 40 (i.e., meets objectively defined amnestic criteria), and positive AD-related CSF biomarkers (CSF $A\beta 1-42/A\beta 1-40$ and p-tau (or total tau) above a pre-determined threshold).

Study Design

This is a randomized double-blind placebo-controlled study of VX-745 (40 mg or placebo) administered twice daily with food for 24 weeks.

Primary endpoints include change in verbal episodic memory immediate and delayed recall, in VX-745-treated patients compared to that in placebo recipients.

Secondary endpoints include change in WMS verbal-paired-associations and visual reproduction, immediate/delayed recall and recognition; MMSE; CDR-SOB; CSF biomarkers (total tau, p-tau, $A\beta 40$, $A\beta 42$).

Example 4

The present example demonstrates effects of VX-745 in reducing EEA1-labeled early endosome numbers and size in a model in vitro system for dementia.

Down's Syndrome (DS, Trisomy 21) derived human fibroblasts provide a robust system for studying Alzheimer's related endosomal dysfunction as one of the Familial Alzheimer's disease (FAD) genes, Amyloid Precursor Protein (APP), is expressed on chromosome 21 and as a result inherently DS individuals overexpress APP and develop an Alzheimer's type dementia as they grow older beyond age 40 (Jiang, Y, et. al., "Alzheimer's-related endosome dysfunction in Down syndrome is Aβ-independent but requires APP and is reversed by BACE-1 inhibition," *PNAS* 107: 1630-1635 (2010)).

Figure 16:
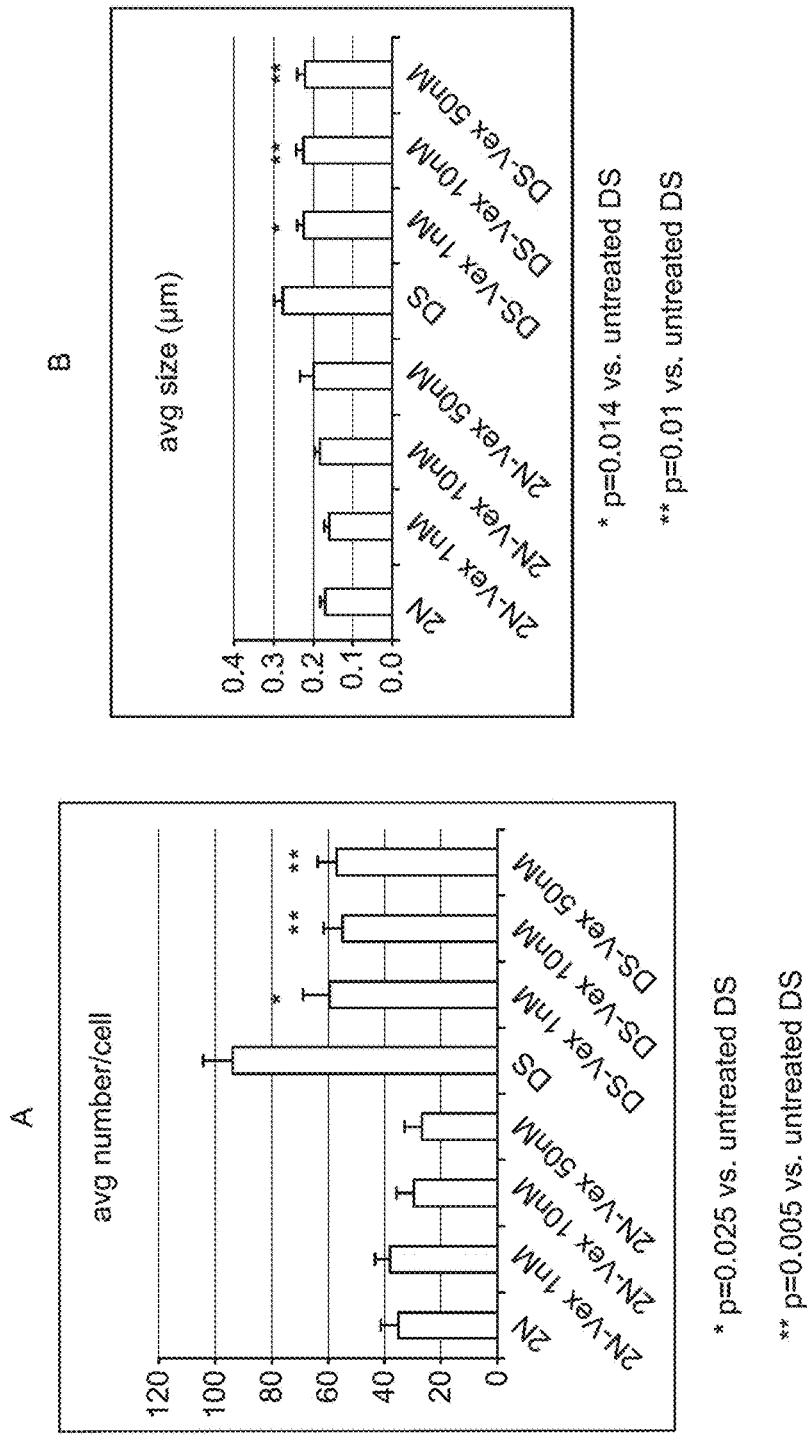
FIG. 16 depicts EEA 1 positive endosomes in 2N (Wild-Type) or DS (Down's Syndrome) human fibroblasts after 24 hours exposure to VX-745. (A) shows average number of endosomes per cell. (B) shows average size of endosomes.

In vitro, DS human fibroblasts show increased numbers and enlarged early endosomes by electron microscopy or by fluorescence staining with antibodies to EEA1 (Early Endosome Antigen 1). 2N and DS (Down's Syndrome) human fibroblasts were incubated with 0, 1, 10, or 50 nM of VX-745 for 24 hours. After incubation, the cells were fixed and incubated with anti-EEA1 antibody to label early endosomes. FIG. 16 depicts EEA1 positive endosomes in 2N (Wild-Type) or'DS (Down's Syndrome) human fibroblasts after 24 hours exposure to VX-745. (A) Shows average number of EEA1-labeled endosomes per cell was higher for DS versus 2N cells and incubation with VX-745 significantly reduced the average number EEA1-labeled endosomes per DS cell. (B) Shows average size of EEA1-labeled endosomes was significantly reduced in DS cells after incubation with VX-745.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method of improving episodic memory in a human subject, the method comprising administering to a subject in need thereof a therapeutically effective amount of VX-745, wherein the subject has mild cognitive impairment (MCI).

2. The method of claim 1, wherein the subject has a neurodegenerative disorder characterized by an increase in the number and/or size of endosomes.

3. The method of claim 1, wherein the therapeutically effective amount of VX-745 provides an average blood concentration of about 8 ng/mL.

4. The method of claim 1, wherein the therapeutically effective amount is achieved by twice daily administration.

5. The method of claim 4, wherein the twice daily administering occurs about 9 to 15 hours apart.

6. The method of claim 5, wherein the twice daily administering occurs about 12 hours apart.

7. The method of claim 1, wherein the administering occurs within about 30 to 60 minutes after the subject consumes food.

8. The method of claim 1, wherein the improvement in episodic memory is measured by one or more of the Mini-Mental State Examination (MMSE), Wechsler Memory Scale (WMS), the Hopkins Verbal Learning Test-Revised (HVLT-R), Clinical Dementia Rating (CDR), the Columbia Suicide Severity Rating Scale (C-SSRS), Alzheimer's Disease Assessment Scale-Cognitive (ADAS-Cog), neuropsychological testing, radiological testing, evaluation of cerebrospinal fluid (CSF), neuroimaging, and combinations thereof.

9. The method of claim 1 wherein an improvement in episodic memory is measured by the Wechsler Memory Scale (WMS).

10. The method of claim 1 wherein an improvement in episodic memory is measured by the Mini-Mental State Examination (MMSE).

* * * * *